United States Patent
Shino et al.

(10) Patent No.: US 7,270,812 B2
(45) Date of Patent: Sep. 18, 2007

(54) PHARMACEUTICAL COMPOSITION FOR TREATMENT OF CANCERS

(76) Inventors: Yuji Shino, 1050-7, Hoshiguki-cho, Chuo-ku, Chiba-shi, Chiba 260-0808 (JP); Kouta Sunouchi, Matsumoto Building 701, 5-33-9, Nakakasai, Edogawa-ki, Tokyo (JP); Takehide Asano, 4-14-11, Masago, Mihama-ku, Chiba-shi, Chiba 261-0011 (JP); Hiroshi Shirasawa, 1-21-20, Tsukushi-za, Yotsukaido-shi, Chiba 284-0026 (JP)

( * ) Notice: Subject to any disclaimer, the term of this patent is extended or adjusted under 35 U.S.C. 154(b) by 60 days.

(21) Appl. No.: 10/911,580

(22) Filed: Aug. 5, 2004

(65) Prior Publication Data

US 2005/0031594 A1    Feb. 10, 2005

Related U.S. Application Data

(60) Provisional application No. 60/493,324, filed on Aug. 8, 2003.

(51) Int. Cl.
*A01N 63/00* (2006.01)
*C12N 7/00* (2006.01)

(52) U.S. Cl. .................. 424/93.6; 424/93.1; 424/93.2; 435/235.1

(58) Field of Classification Search ............... 424/93.1, 424/93.2, 93.4, 93.6, 199.1, 9.6; 435/235.1, 435/239, 320.1, 456, 69.3, 5
See application file for complete search history.

(56) References Cited

U.S. PATENT DOCUMENTS 6,344,195 B1    2/2002   Lee et al.

FOREIGN PATENT DOCUMENTS

| JP | 2003-176236 A | 6/2003 |
|---|---|---|
| WO | WO99/18799 A1 | 4/1999 |
| WO | WO 00/11201 A1 | 3/2000 |
| WO | WO 00/62735 A2 | 10/2000 |
| WO | WO 02/00233 A2 | 1/2002 |
| WO | WO 02/076468 A1 | 10/2002 |

OTHER PUBLICATIONS

Etoh et al., "Oncolytic Viral Therapy for Human Pancreatic Cancer Cells by Reovirus," Clinical Cancer Research, vol. 9 No. 3, pp. 1218-1223 (Mar. 2003).*
Ries et al., "Oncolytic viruses for the treatment of cancer: current strategies and clinical trials," Drug Discovery Today, vol. 9 No. 17, pp. 759-768 (Sep. 2004).*
Sherman and Griffin, "Pathogenesis of encephalitis induced in newborn mice by virulent and avirulent strains of Sindbis virus," Journal of Virology, vol. 64 No. 5, pp. 2041-2046 (May 1990).*
Unno et al., "Oncolytic Viral Therapy for Cervical and Ovarian Cancer Cells by Sindbis Virus AR339 Strain," Clinical Cancer Research, vol. 11 No. 12, pp. 4553-4560 (Jun. 2005).*
Jen-Chieh Tseng et al.; Journal of the National Cancer Institute; vol. 94, No. 23; Dec. 4, 2002; pp. 1790-1801.
Alison J. Mastrangelo et al.; Cytotechnology; vol. 22, No. 1-3; 1996; pp. 169-178.
Kuo-I Lin et al.; The Journal of Biological Chemistry; vol. 274, No. 19; May 7, 1999; pp. 13650-13655.
Diane E. Griffin, M.D., PH.D: et al.; Virology; vol. 1, Fourth Edition; Chapter 30; pp. 917-962. 2001.

* cited by examiner

*Primary Examiner*—Bruce R. Campell
*Assistant Examiner*—Zachariah Lucas
(74) *Attorney, Agent, or Firm*—Birch, Stewart, Kolasch & Birch, LLP

(57) ABSTRACT

The present invention relates to a pharmaceutical composition for treatment of cancers containing Sindbis virus as an active ingredient, a method for treatment of cancers, which comprises administering a therapeutically effective amount of Sindbis virus to a mammal having cancers, a method for identifying cancers, which includes introducing Sindbis virus into an animal, thereby detecting a Sindbis virus protein or Sindbis virus RNA in vital tissues of the above animal, a method of identifying cancers, which includes introducing into an animal Sindbis virus having a reporter gene incorporated therein, thereby, detecting the product of the reporter gene in vital tissues of the animal, and a method of identifying cancers, which includes detecting a increase in antibody titer to the Sindbis virus protein or the product of the reporter gene in the aforementioned animals.

8 Claims, 28 Drawing Sheets

(6 of 28 Drawing Sheet(s) Filed in Color)

Fig. 4
Cytopathic effects of Sindbis virus and reovirus on pancreatic cancer cells
C: control  R: reovirus  S: Sindbis virus  W: Sindbis+reovirus
Bx-PC
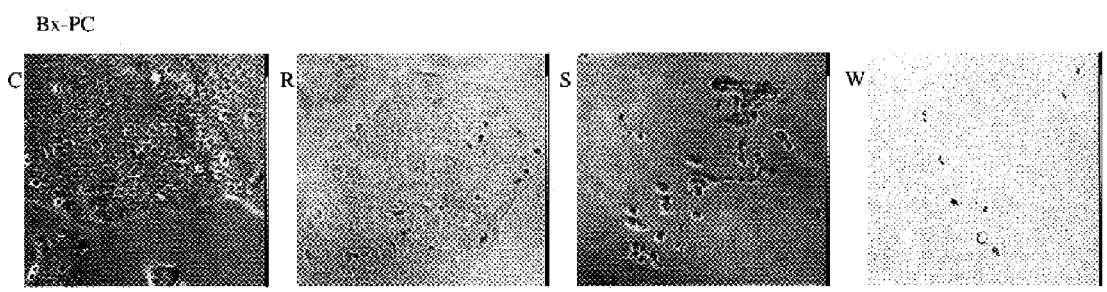
SUIT-2
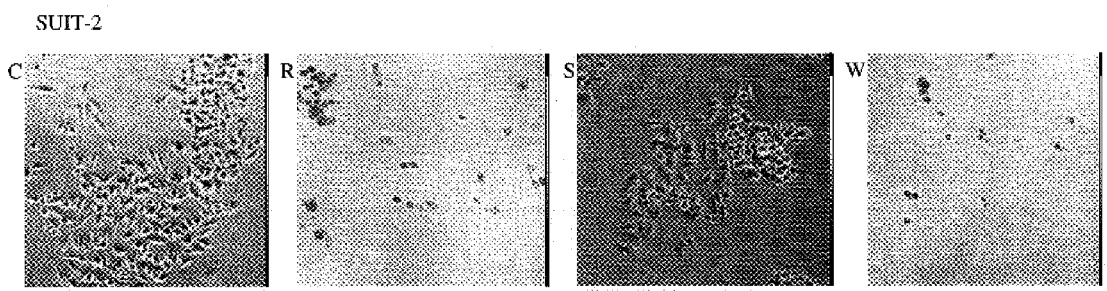

Fig. 13 SUIT-2

PANC-1
Tumor size (cm)

MIAPaCa-2

Fig. 21 TTn

PHARMACEUTICAL COMPOSITION FOR TREATMENT OF CANCERS

This Non-provisional application claims priority under 35 U.S.C. § 119(e) on U.S. Provisional Application No(s). 60/493,324 filed on Aug. 8, 2003, the entire contents of which are hereby incorporated by reference.

TECHNICAL FIELD

The present invention relates to a pharmaceutical composition for treatment of cancers containing Sindbis virus as an active ingredient, and a method for treatment of cancers, which comprises administering a therapeutically effective amount of Sindbis virus to a mammal having cancers.

BACKGROUND ART

A typical example of virus used to date as an agent for treatment of cancers is adenovirus, which is a vector for gene therapy. Adenovirus, however, merely functions as a vector for gene therapy, but a cytotoxic gene introduced therein is actually involved in treatment of cancers. Essentially, viruses infect specific cells to grow therein, thereby causing cell death to the infected cells with morphological changes, which are called cytopathic effects (CPEs). In recent years, a special virus, denominated oncolytic virus (wherein "onco" refers to cancer and "lytic" refers to lysis), has been known to exist. Oncolytic viruses grow in specific cancer cells, thereby exhibiting the strong CPE specific thereto and destroying them. The viruses, however, neither grow nor exhibit CPE in normal cells. To date, oncolytic viruses such as a reovirus specific to Ras-activated cancer cells (U.S. Pat. No. 6,344,195), an adenovirus variant specific to anticancer protein p53 defective cancer cells (DL1520; ONYX-015) (Post LE, Curr Opion Investig Drugs, 3(12), 1768-1772, 2000.), and a herpes virus variant specific to brain tumors (G207) (Toda M., Rabkin S D., Martuza R L., Hum Gene Ther, 9(15), 2177-2185, 1988) have been reported. Since oncolytic viruses exert their cytotoxity only for cancer cells but are harmless to normal cells, "anticancer virus therapy," which is a new method for treatment of cancers employing the virus, is been becoming established. In contrast to surgery, which is a mainstream of current cancer treatment, the "anticancer virus therapy" is expected to be a less-invasive and more effective treatment. However, oncolytic viruses known heretofore have limited effects. In the case of the reovirus described above, for example, the virus can target only Ras-activated cancer cells, which account for approximately two-thirds of human cancers. Thus, the scope of application thereof is limited.

On the other hand, Sindbis virus is an RNA virus belonging to the genus *Alphavirus* of family *Togaviridae*, and is transmitted by mosquitoes that infect birds or mammals. Sindbis virus is a virus having a spherical shape with a diameter of approximately 40 nm to 80 nm, and it contains a single-stranded RNA genome and a nucleocapsid with a regular dodecahedron shape in its envelope. Sindbis virus AR339 strain was isolated from the mosquitoes (*Culex pipiens* and *C. univittatus*) in the north of Cairo, Egypt, in 1952 (Taylor, R M and H S Hurlbut; "Isolation of coxsackie-like viruses from mosquitoes" J. Egypt. Med. Assoc., 36, 489-494, 1953, etc.). Sindbis virus has so far been known to cause cytopathic effects upon various established mammalian cell lines (Griffin D E., 2001, Alphaviruses, 917-962, In Knipe D M and Howley P M (ed.), Fields virology, 4$^{th}$ ed., Lippincott-Raven Publishers, Philadelphia, Pa.), though its high specificity to cancer cells has not been reported. As in the case of adenovirus, there is nothing but an example that Sindbis virus was confirmed to have antitumor effects as a viral vector used for introduction of foreign genes (Jen-Chieh Tseng et al., "In Vivo Antitumor Activity of Sindvis Viral Vectors" Journal of the National Cancer Institute 94 (23), 1790-1801, Dec. 4, 2002).

DISCLOSURE OF THE INVENTION

It is an object of the present invention to find a new oncolytic virus and to utilize it for treatment of cancers.

Over the course of studies regarding oncolytic viruses, the present inventors have found that a Sindbis virus AR339 strain causes cytopathic effects upon various established mammalian cell lines, but not upon normal human primary culture keratinocytes. Thus, the inventors hypothesized that Sindbis virus has tumor cell-specific effects, and then conducted the in vitro and in vivo examinations. As a result, the inventors confirmed that the Sindbis virus has cytopathic effects upon various cancer cell lines in vitro, and that reduction in tumor size or disappearance of tumor caused by the selective proliferation of the virus in a tumor takes place in vivo. Thus, they found that Sindbis virus is an oncolytic virus, which is effective for treatment of cancers. The present invention has been completed based on these findings.

That is to say, the present invention includes the following features:

(1) A pharmaceutical composition for treating cancers, which comprises Sindbis virus as an active component.

(2) The pharmaceutical composition of (1) above, which comprises at least one strain of Sindbis virus.

(3) The pharmaceutical composition of (1) above, wherein the Sindbis virus is Sindbis virus AR339.

(4) The pharmaceutical composition of (1) above, which further comprises another oncolytic virus.

(5) The pharmaceutical composition of (4) above, wherein the other oncolytic virus is a reovirus.

(6) The pharmaceutical composition of (1) above, wherein the cancer is selected from the group consisting of cervical cancer, esophageal cancer, gastric cancer, pancreatic cancer, liver cancer, lung cancer, parotid cancer, salivary gland cancer, colon cancer, breast cancer, renal cancer, prostate cancer, brain cancer, skin cancer, adrenal cancer, oral cancer, rectal cancer, endometrial cancer, thyroid cancer, ovarian cancer, laryngeal cancer, leukemia, and malignant lymphoma.

(7) A method for the treatment of cancers, which comprises administering to a mammal having cancers a therapeutically effective amount of Sindbis virus.

(8) The method of (7) above, wherein at least one strain of Sindbis virus is administered.

(9) The method of (7) above, wherein the Sindbis virus is Sindbis virus AR339.

(10) The method of (7) above, wherein the Sindbis virus is administered concurrently with another oncolytic virus.

(11) The method of (10) above, wherein the other oncolytic virus is a reovirus.

(12) The method of (7) above, wherein the cancer is selected from the group consisting of cervical cancer, esophageal cancer, gastric cancer, pancreatic cancer, liver cancer, lung cancer, parotid cancer, salivary gland cancer, colon cancer, breast cancer, renal cancer, prostate cancer, brain cancer, skin cancer, adrenal cancer, oral cancer, rectal cancer, endometrial cancer, thyroid cancer, ovarian cancer, laryngeal cancer, leukemia, and malignant lymphoma.

(13) The method of (7) above, wherein the Sindbis virus is administered intravenously, intraarterially, intramuscularly, intraperitoneally, subcutaneously, topically, intratumorally, orally, transdermally, rectally, intravaginally, intranasally, or sublingually.

(14) The method of (7) above, wherein 0.01 to $1 \times 10^{15}$ plaque forming units (PFU) of Sindbis virus per kilogram of body weight are administered.

(15) A method for identifying cancers, which comprises introducing Sindbis virus into an animal, thereby detecting metabolic changes in the above animal.

(16) A method for identifying cancers, which comprises introducing Sindbis virus into an animal, thereby detecting a Sindbis virus protein or Sindbis virus RNA in vital tissues of the above animal.

(17) A method of identifying cancers, which comprises introducing into an animal Sindbis virus having a reporter gene incorporated therein, thereby detecting the product of the above reporter gene in vital tissues of the above animal.

BRIEF DESCRIPTION OF DRAWINGS

The patent or application file contains at least one drawing executed in color. Copies of this patent or patent application publication with color drawing(s) will be provided by the office upon request and payment of the necessary fee.

FIG. 4 shows the cytopathic effects of Sindbis virus (photographs taken at 72 hours after virus infection) upon pancreatic cell lines (BxPC-3, SUIT-2.) (C: control (no virus infection); R: reovirus infection (1 MOI); S: Sindbis virus infection (1 MOI); W: reovirus infection (0.5 MOI)+Sindbis virus infection (0.5 MOI)).

Figure 1:
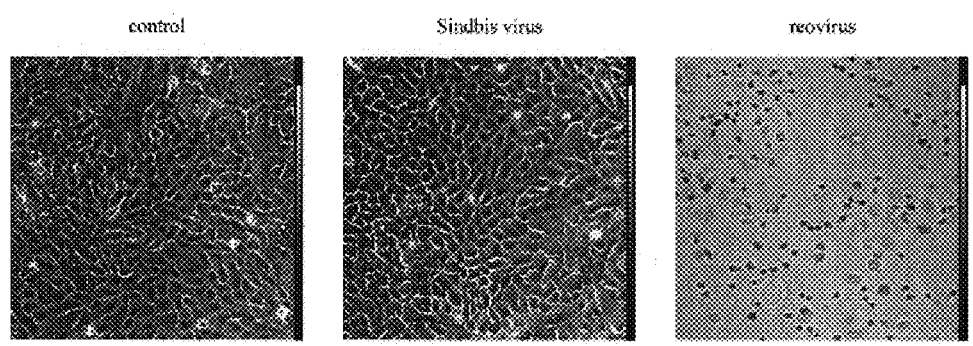
FIG. 1 shows the cytopathic effects of Sindbis virus (photographs taken at 48 hours after virus infection) upon primary human keratinocytes (control: no virus infection; Sindbis virus: Sindbis virus infection; reovirus: reovirus infection).

The present invention will be described in detail below. This patent application claims priority based on U.S. Patent Application (provisional) No. 60/493,324 filed on Aug. 8, 2003, and includes part or all of the contents as disclosed in the description and/or the drawings thereof.

The term "Sindbis virus" used in the present invention includes any virus belonging to the genus Alphavirus, Sindbis virus. Typical examples of Sindbis viruses preferably used in the present invention include, but are not limited to, Sindbis virus AR339 strain.

It is to be noted that there has been no report that Sindbis virus AR339 strain causes serious diseases for humans, and thus, the safety thereof has been established.

Further, Sindbis virus AR339 strain may be used in combination with other strains (for example, SR86 (South Africa), and SV-Peleg (Israel)). The origin of Sindbis virus is not particularly limited.

Sindbis virus AR339 strain has been conserved in a Dulbecco's modified Eagle medium supplemented with 2% fetal bovine serum or with 50 mM Tris-HCl (pH 7.4), 100 mM NaCl, and 1 mM EDTA, at −80° C., at the Department of Molecular Virology (E2) Graduate School of Medicine, Chiba University, Japan.

Sindbis virus itself has a significant antitumor activity. The virus exerts more excellent antitumor activity with the combined use of other viruses, including reportedly oncolytic viruses, such as reovirus, adenovirus, herpes simplex virus, newcastle disease virus, poliovirus, vesicular stomatitis virus, or measles virus. Reovirus is particularly preferable among the above viruses.

The term "antitumor activity" herein includes a selective-growth-inhibitory effect and a damage effect on tissues or cells of malignant tumors, and reduction or disappearance of tumor tissues or cells. It shall be construed in the broadest sense.

Sindbis virus has the antitumor activities described above. It may be administered directly to mammals of interest. However, in general, Sindbis virus, as an active ingredient, may be mixed with pharmacologically and pharmaceutically acceptable additives, so as to prepare various types of formulations and to provide them as pharmaceutical compositions for treatment of cancers.

The form of formulation of Sindbis virus includes oral or parenteral preparations such as solid medicines (e.g., tablets, powders, granules, and capsules), liquid preparations for internal use (e.g., suspensions, syrups, and emulsions), liquid preparations for external use (e.g., injectants, sprays/aerosols, inhalants, and liniments), injections (intravenous, intramuscular, intraperitoneal, and subcutaneous injections), drops, and suppositories. Injection of Sindbis virus is preferably provided in the form of unit dose ampule or in the form of a multiple doses package. In addition, the virus in a preparation may be an infectious virus (live virus) or an inactivated virus.

In any preparations, Sindbis virus is preferably stabilized and more preferably exists uniformly. Examples of a method for stabilizing live Sindbis virus may include a method of dispersing the virus in an anhydrous medium, a method of mixing a stabilizer into a preparation, and a method of coating the virus. The method to be employed is appropriately selected depending on the form of a formulation.

A pharmacologically and pharmaceutically acceptable additive can be employed depending on each dosage form. Examples of such an additive may include an excipient, a disintegrator, a binder, a lubricant, a wetting agent, a coating agent, a stabilizer, a diluent, a base, a resolvent, a solubilizer, an isotonizing agent, a pH regulant, a propellant, a binder, or the like.

The content of Sindbis virus in the pharmaceutical components described above is not particularly limited, as long as it is appropriate as unit dose for human patients and other mammals and it imparts desired therapeutic effects. The content, for example, may be exemplified as between 1.0 pfu and $1.0\times10^{13}$ PFU, and it may be optionally adjusted based on the route of administration, dosage form, and target disease.

In the present specification, the term "cancer" means a generic name of malignant tumor (or malignant neoplasma), including not only solid tumors such as tumors developed on epithelial tissues or sarcomas developed on connective tissues (bone, muscle, cartilage, sinew, ligament, adipose, and blood vessel), but also all non-solid tumors such as leukemia that are malignant tumors in the blood system and lymphomas. Thus, target diseases to which a pharmaceutical composition for treatment of cancers of the present invention can be applied include, but are not limited to, cervical cancer, esophageal cancer, gastric cancer, pancreatic cancer, liver cancer, lung cancer, parotid cancer, salivary gland cancer, colon cancer, breast cancer, renal cancer, prostate cancer, brain cancer, skin cancer, adrenal cancer, oral cancer, rectal cancer, endometrial cancer, thyroid cancer, ovarian cancer, laryngeal cancer, leukemia, and malignant lymphoma. Sindbis virus is particularly effective for tumors developed on stratified squamous epithelium in the skin, mouth, esophagus, vaginal epithelium, and corneal epithelium (squamous-cell carcinoma); adenocarcinomas such as gastric cancer or pancreatic cancer; and liver cancer.

Furthermore, Sindbis virus is effective for metastatic or recurrent cancers, other than primary cancers. It can be applied regardless of the stage of cancer (early cancer or advanced cancer).

Sindbis virus is administered at an effective dose for treating cancers to mammals having cancers, such as humans, dogs, cats, sheep, goats, bovines, horses, and pigs. The term "effective dose for treating cancers" refers to a dose causing suspension of cancer cell growth, reduction in tumor size, and disappearance of tumor involving the administration of Sindbis virus to growing cancer cells. The specific dose should be appropriately increased or decreased depending on the route of administration, age and body weight of patient, tumor type and malignancy, and presence or absence of metastasis or recurrence. In general, the administration dose of Sindbis virus for an adult may be taken at once or several times a day within the range of 0.01 to $1\times10^{15}$ PFU/kg body weight, preferably $1.0\times10^{2}$ to $1.0\times10^{13}$ PFU/kg body weight, and more preferably $1.0\times10^{7}$ to $1\times10^{10}$ PFU/kg body weight.

When Sindbis virus is administered in combination with other oncolytic viruses, the efficacy thereof can be confirmed even at doses reduced by about two orders of magnitude from those described above.

Sindbis virus can be administered orally or parentally using the above pharmaceutical compositions prepared in various dosage forms. Sindbis virus is administered, for example, intravenously, intraarterially, intramuscularly, intraperitoneally, subcutaneously, topically, intratumorally, orally, transdermally, rectally, intravaginally, intranasally, or sublingually. Specifically, in the case of a solid tumor developed in organs which is effortlessly accessible by surgery, the virus may be topically injected to such tumor or to the vicinity thereof using a stereotaxic needle or the like, and in the case of non-solid tumor such as leukemia, brain tumor which is hardly accessible by surgery, or metastatic cancer, the virus may be intravenously injected. In other cases, the virus can be used by appropriately selecting the above routes based on the type or site of tumor.

Sindbis virus may be administered either once or several times a day. In the latter case, the virus may be continuously administered, for example, at an interval of several days or several weeks.

The treatment of cancers using Sindbis virus may be combined with publicly known methods for treating cancers, such as surgery, chemotherapy, or radiotherapy. Also, a virus which is a non-oncolytic virus, an antigen which disturbs the immune response of the host (BCG antigen of tubercle bacillus), and immunosuppressive agents such as steroids or cyclosporin A may be used in combination with Sindbis virus for treating cancers, as long as the expected objects can be achieved.

Sindbis virus selectively infects cancer cells and grows therein. In a cell infected with Sindbis virus, metabolism necessary for virus proliferation, e.g., virus genome replication and virus gene expression, becomes active. Accordingly, in vivo identification of cancer (cells or tissues) can be realized by administering Sindbis virus to an animal to detect change in metabolism of sugar, amino acid, etc. in vital samples of the animal or expression of a Sindbis virus protein, or the like. Further, identification of cancer can also be carried out by using Sindvis virus into which a reporter gene or the like has been inserted for genetic recombination and by detecting the expression of the above gene.

The term "identification of cancer" herein includes diagnosis of the presence or absence of cancer, localization of cancer, and the degree of progression of cancer. Furthermore, the term "animal" can be understood to refer to the aforementioned mammals including humans. Administration of Sindbis virus may be performed intravenously, intra-arterially, intraperitoneally, or via any other routes. Vital samples used herein may include tissues of the digestive system, such as liver, stomach, large intestine, or pancreas, tissues of any other organs in the body, such as uterus, prostate, or kidney, squamous cell tissues, cells derived from the aforementioned organs, blood, and body fluid such as lymph.

Identification of cancer using Sindbis virus can be specifically performed by methods such as diagnostic imaging, pathologic diagnosis, or serodiagnosis.

Diagnostic imaging involves preparing Sindbis virus wherein a reporter gene has been incorporated downstream of a virus promoter thereof, administering this virus to an animal, and detecting the expression of the reporter gene using existing diagnostic imaging equipments (e.g., positron emission tomography (PET), MRI, CT, echography, endoscopy, and stereoscopy) or using future expected practical-in-use diagnostic imaging (e.g., highly sensitive fluorescence detector). Otherwise, it is also possible to administer wild-type Sindbis virus to an animal and to examine changes in metabolism of sugar, amino acid, etc. in cancer cells using PET or the like.

Pathologic diagnosis can be performed by detecting the expression of a virus protein in cells or tissues by an immunostaining method, Western blot (see FIG. 19), or the like, or by detecting virus RNA by RT-PCR, Northern blot, or the like. In the case of employing a recombinant virus into which a reporter gene has been incorporated, identification of cancer can be carried out by detecting a product of the incorporated gene by the methods described above, or by measuring activity of the gene product. For example, as shown in examples described later, identification of cancer can be carried out by detecting the expression of a green fluorescent protein (GFP) with a fluorescence microscope or equipment for GFP quantification (e.g., Wallac 1420 ARVOsx; Perkin Elmer) (see FIG. 28).

Serodiagnosis can be performed by quantifying virus RNA in serum by RT-PCR, or by measuring an antibody titer to a Sindbis virus protein. With use of recombinant Sindbis virus into which a reporter gene has been incorporated, cancer can also be identified by quantification of the incorporated gene expression by RT-PCR, titration of the gene product, or measurement of the activity of the product.

In the above techniques, a reporter gene is not limited, but various kinds of reporter genes can be employed in accordance with a detection method. For example, a green fluorescent protein (GFP) gene can be used for fluorescence observation, and a herpes simplex virus type 1 thymidine kinase (HSV-tk) gene or dopamine D2 receptor gene can be used for PET. Alternatively, a luciferase gene, chloramphenicol acetyltransferase (CAT), or β-galactosidase gene may also be used.

Furthermore, a method of labeling wild-type Sindbis virus with radioisotopes, fluorescent dyes, enzymes, or the like and detecting it can be included as a preferred embodiment for diagnostic imaging or pathologic diagnosis.

BEST MODE FOR CARRYING OUT THE INVENTION

The present invention will be specifically described in the following examples. However, these examples are not intended to limit the scope of the present invention.

Primary human keratinocytes used in the following examples were isolated from human esophageal, cervical, and gingival tissues as described previously (Sashiyama et al., Int. J. onco. 19: 97-103, 2001), and keratinocytes derived from neonatal human foreskins were purchased from the biomedical department of Kurabo Industries, Ltd. (Osaka, Japan).

EN60 cells were established previously by the immortalization of primary culture human esophageal keratinocytes with human papillomavirus type 16 (HPV16) E6 and E7 (Sashiyama et al., Int. J. onco. 19: 97-103, 2001).

Primary culture keratinocytes and immortalized keratinocytes (EN60) were grown in a serum-free keratinocyte growth medium (KGM, Clonetics, San Diego, Calif.).

Esophageal cancer cell lines (YES-6 and TTn) and a cervical cancer cell line (C33A) were grown in RPMI 1640 containing 10% fetal bovine serum (FBS). Vero and BHK-21 cells were cultured in an Alpha minimal essential medium (α-MEM) supplemented with 10% FBS.

Sindbis virus (SIN) strain AR339 were previously provided from the National Institute of Infectious Diseases (Tokyo, Japan). The virus were propagated in primary chicken embryo fibroblast (CEF) cells and then passaged several times on Vero cells. This virus became our laboratory stock.

Sindbis virus TR339-GFP/2A stably expressing Green fluorescent protein (GFP) was derived from cDNA clone pTR339-GFP/2A (Thomas et al., J. Virol. 77: 5598-5606), which was kindly provided by H. W. Heidner, University of Texas (San Antonio, U.S.A.).

cDNA clones were linearized by digestion with XhoI, and runoff transcripts were produced by using SP6 RNA polymerase. The RNA transcripts were then electroporated into C33A cells, and a virus-containing growth medium was collected at 48 hours after the electroporation and frozen at −70° C.

EXAMPLE 1

In Vitro Examination of Cytopathic Effects

Test cell lines were individually inoculated into each well of a 24-well plate ($1\times10^5$ cells per well) and subjected to infection with Sindbis virus at a multiplicity of infection (MOI) of 1, $10^{-1}$, and $10^{-2}$. For comparison, test cell lines were infected with reovirus at the same level of MOI. As a control, control wells were prepared without virus infection.

Figure 2:
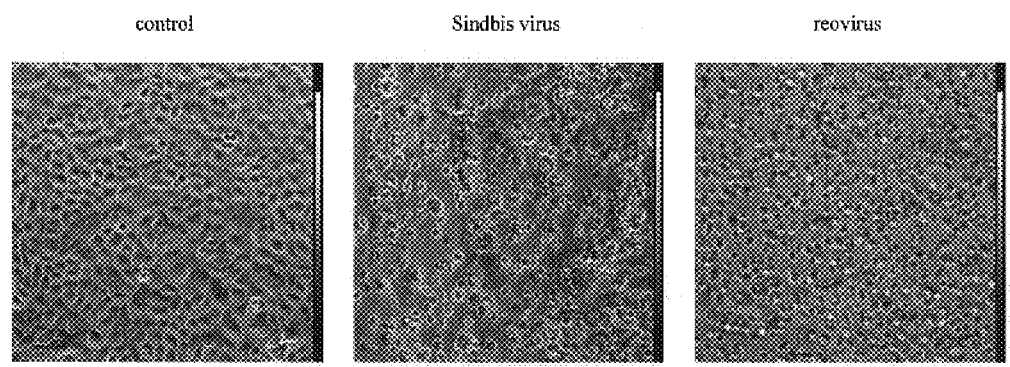
FIG. 2 shows the cytopathic effects of Sindbis virus (photographs taken at 48 hours after virus infection) upon immortalized human keratinocytes (EN60) (control: no virus infection; Sindbis virus: Sindbis virus infection; reovirus: reovirus infection).
Figure 3:
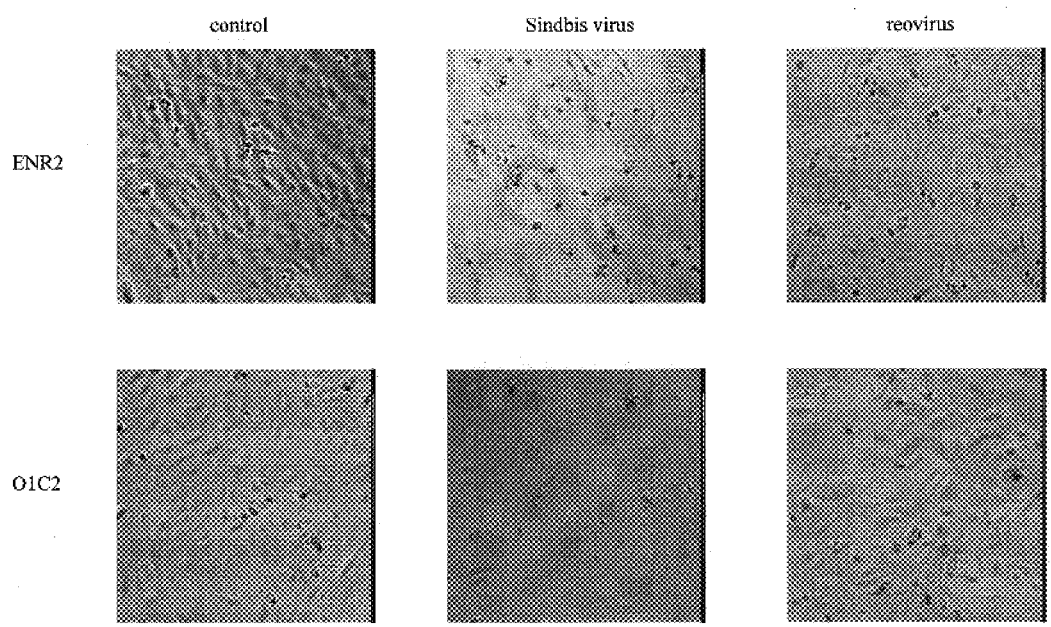
FIG. 3 shows the cytopathic effects of Sindbis virus (photographs taken at 48 hours after virus infection) upon serum-resistant immortalized human keratinocytes (ENR2, O1C2) (control: no virus infection; Sindbis virus: Sindbis virus infection; reovirus: reovirus infection).
Figure 5:
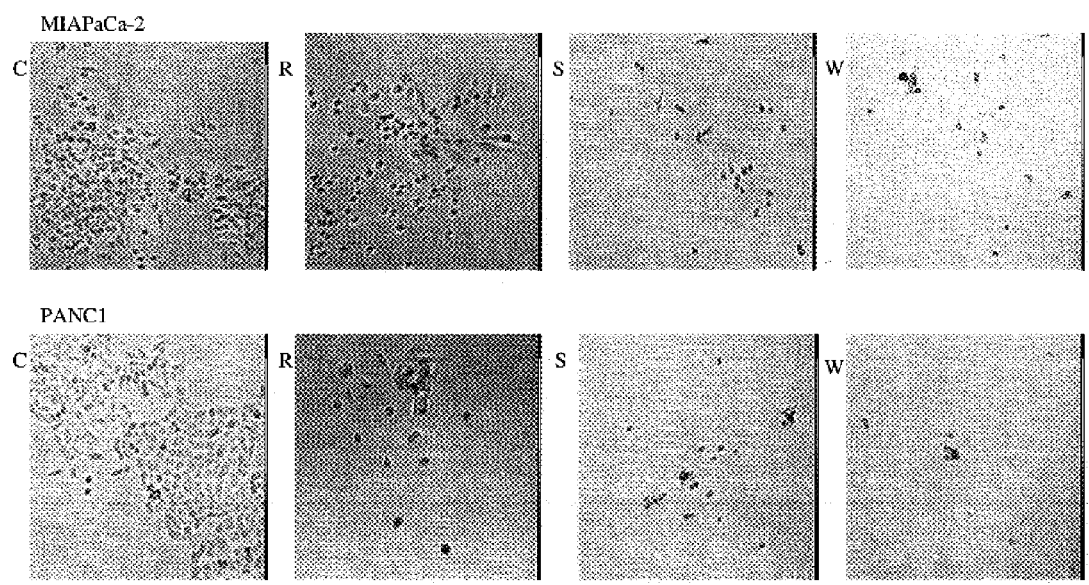
FIG. 5 shows the cytopathic effects of Sindbis virus (photographs taken at 72 hours after virus infection) upon pancreatic cell lines (MIAPaCa-2, PANC-1) (C: control (no virus infection); R: reovirus infection (1 MOI); S: Sindbis virus infection (1 MOI); W: reovirus infection (0.5 MOI)+ Sindbis virus infection (0.5 MOI)).
Figure 6:
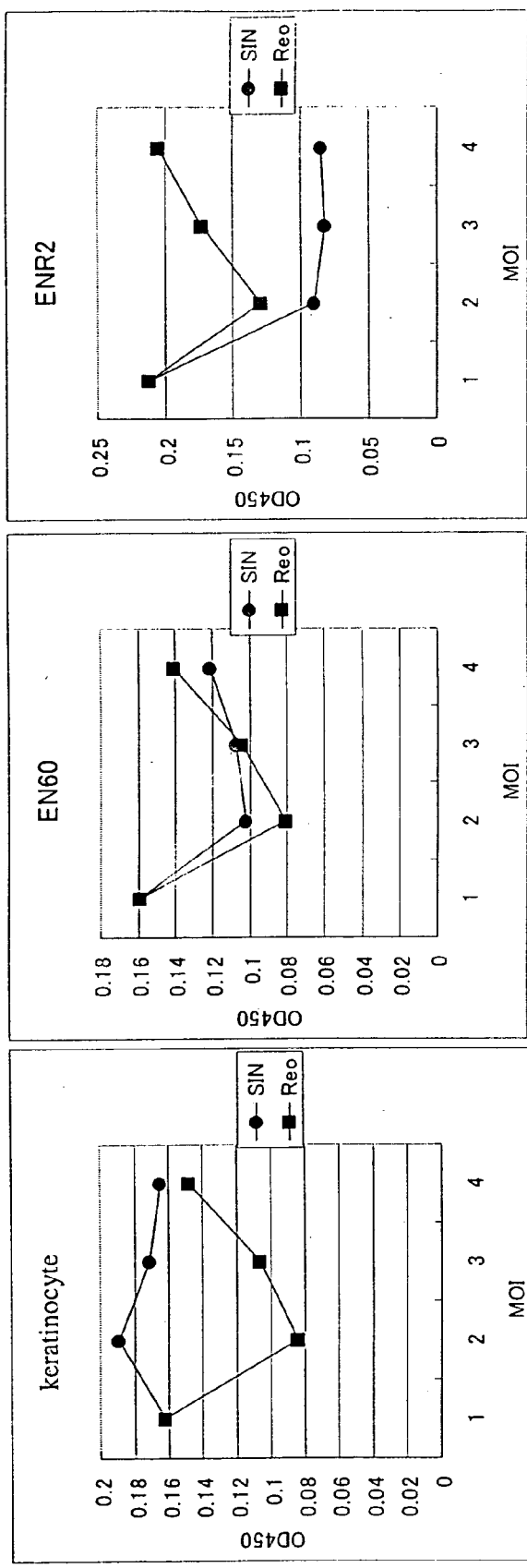
FIG. 6 shows a graph of absorbance at 48 hours after infection with Sindbis virus of primary human keratinocytes (keratinocyte), immortalized human keratinocytes (EN60), and serum-resistant immortalized human keratinocytes (ENR2) (1: control (no infection); 2: 1 MOI; 3: 0.1 MOI; 4: 0.01 MOI).

Sindbis virus did not have cytopathic effects (CPEs) on normal culture primary human keratinocytes derived from human esophagus, foreskin, and uterine cervix (FIG. 1: picture taken at 48 hours after virus infection of 1 MOI, and FIG. 6 (left)). However, Sindbis virus had strong cytopathic effects on immortalized human keratinocytes (EN60) obtained by introducing E6 and E7 genes of human papilloma virus type 16 into human keratinocytes, thereby expressing them, and on serum-resistant immortalized human keratinocytes (ENR2 and OIC2) acquiring resistance to serum supplementation (see H. Sashiyama et al., Cancer Letters 177, 21-28, 2002) (FIGS. 2 and 3: photographs taken at 48 hours after virus infection of 1 MOI). An experiment using pancreatic cancer cell lines (SUIT-2, BxPC-3, PANC-1, and MIAPaCa-2) was further conducted in the same manner. In this case, Sindbis virus exhibited strong cytopathic effects as in the case of reovirus. A combined use of Sindbis virus and reovirus enhanced the cytopathic effects thereof (FIGS. 4 and 5: photographs taken at 72 hours after virus infection of 1 MOI).

Figure 7:
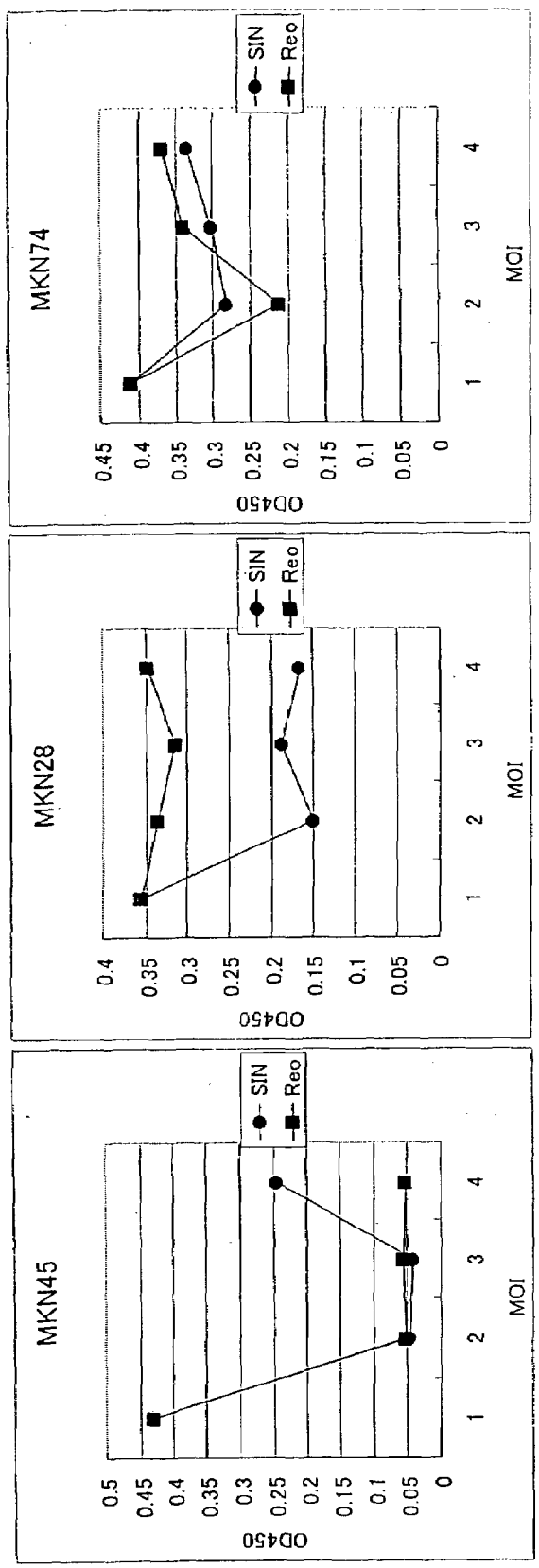
FIG. 7 shows a graph of absorbance at 48 hours after infection with Sindbis virus of gastric cancer cell lines (MKN45, MKN28, and MKN74) (1: control (no infection); 2: 1 MOI; 3: 0.1 MOI; 4: 0.01 MOI).
Figure 8:
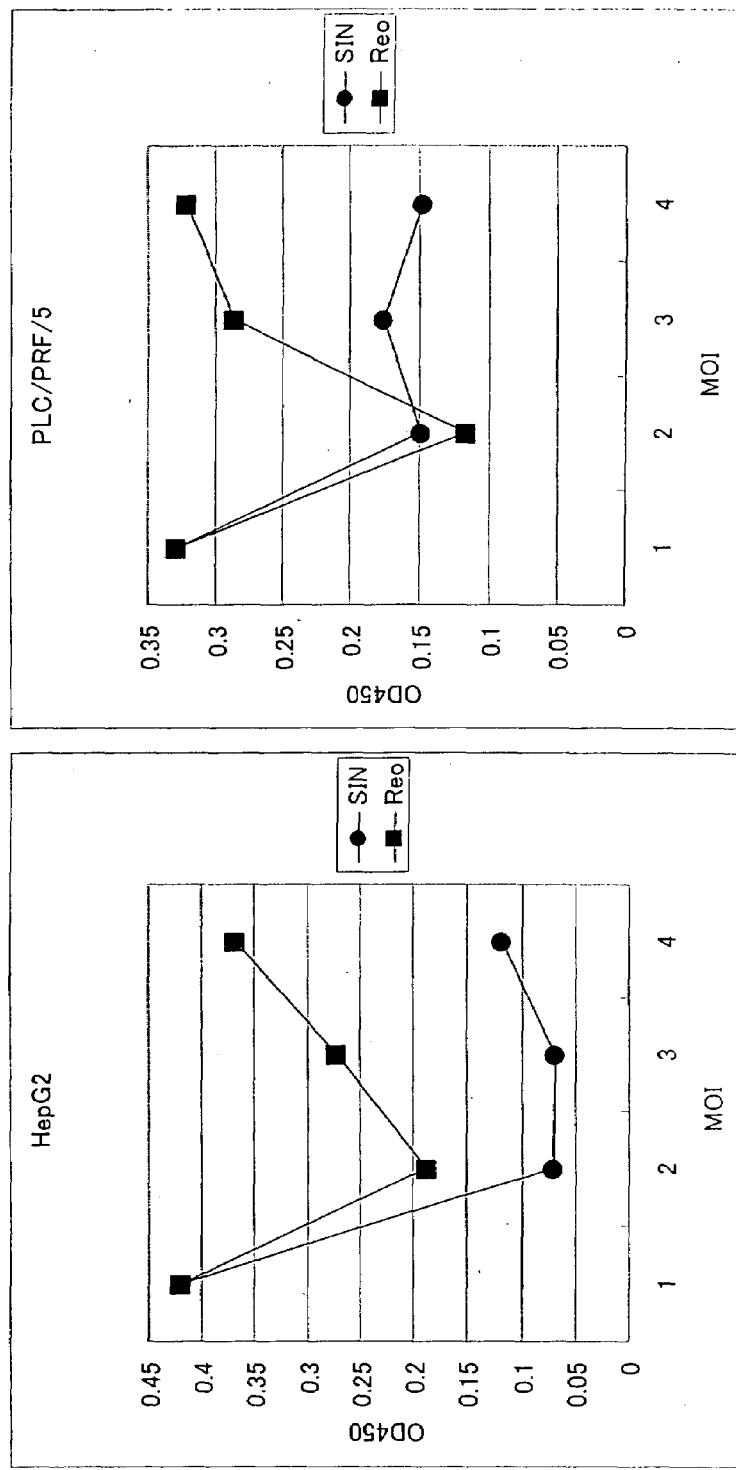
FIG. 8 shows a graph of absorbance at 48 hours after infection with Sindbis virus of liver cancer cell lines (HepG2 and PLC/PRF/5) (1: control (no infection); 2: 1 MOI; 3: 0.1 MOI; 4: 0.01 MOI).
Figure 9:
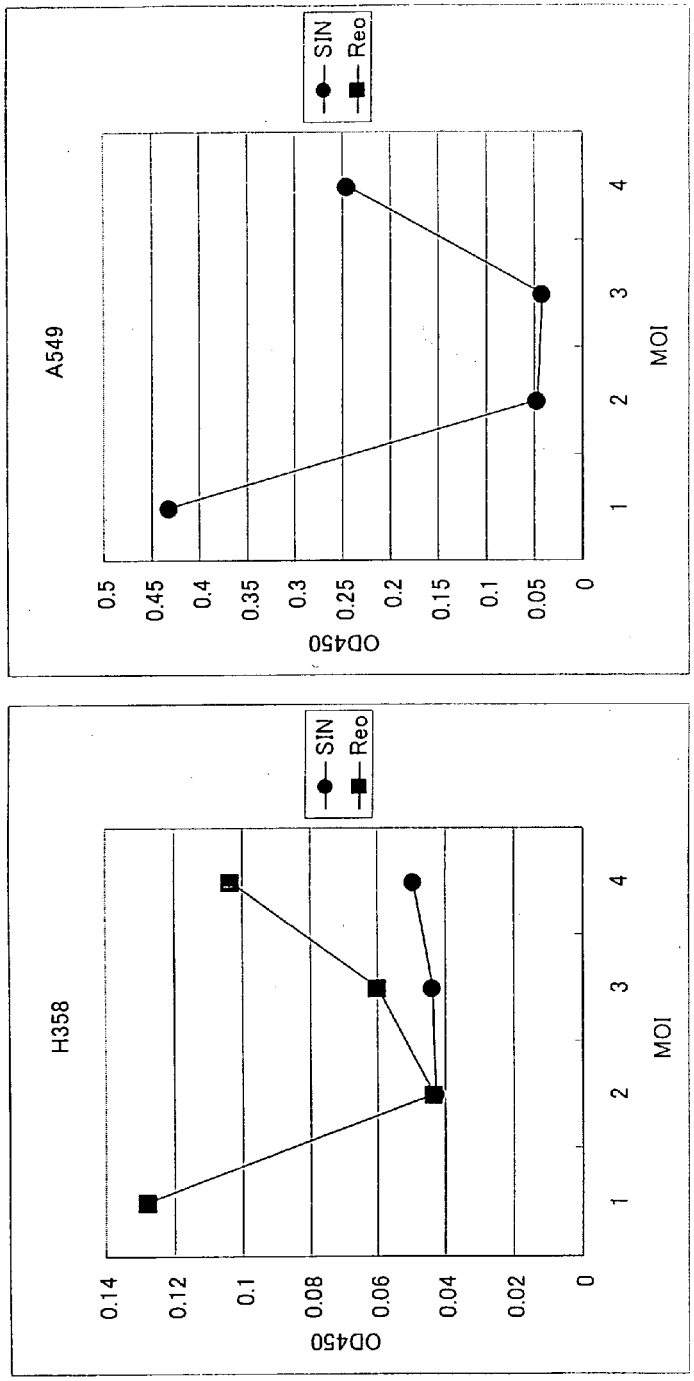
FIG. 9 shows a graph of absorbance at 48 hours after infection with Sindbis virus of lung cancer cell lines (H358 and A549) (1: control (no infection); 2: 1 MOI; 3: 0.1 MOI; 4: 0.01 MOI).
Figure 10:
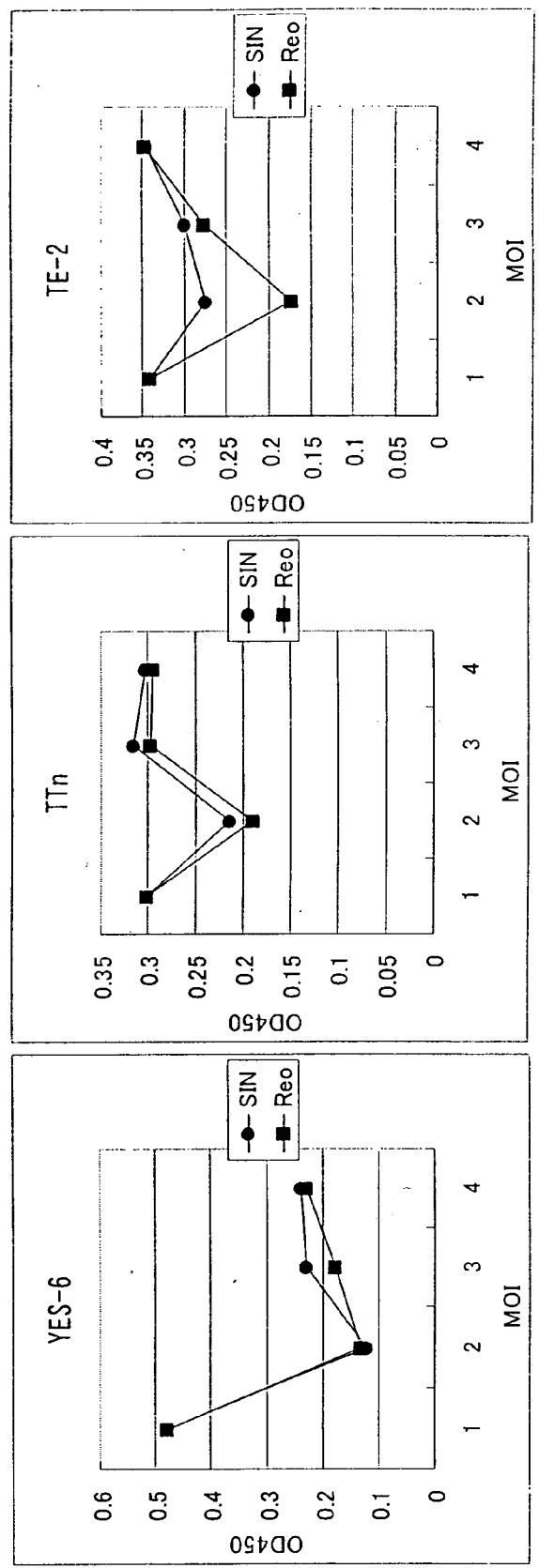
FIG. 10 shows a graph of absorbance at 48 hours after infection with Sindbis virus of esophageal cancer cell lines (YES-6, TTn, and TE-2) (1: control (no infection); 2: 1 MOI; 3: 0.1 MOI; 4: 0.01 MOI).
Figure 11:
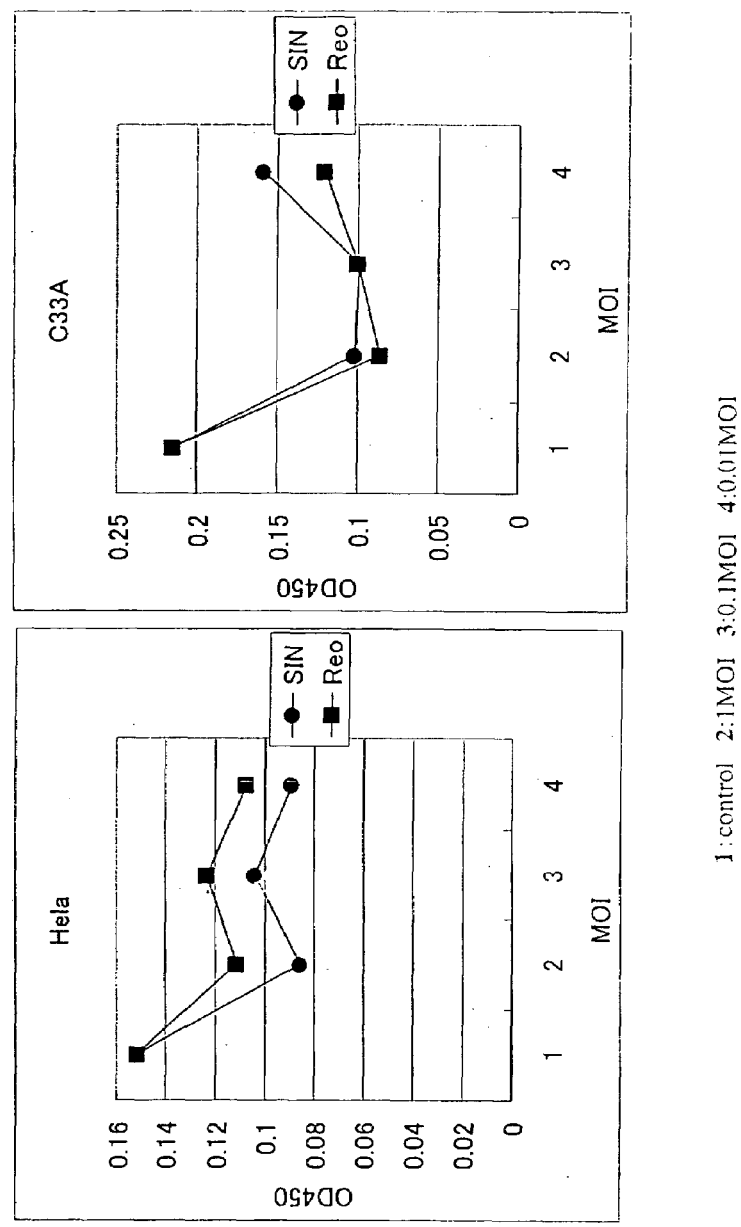
FIG. 11 shows a graph of absorbance at 48 hours after infection with Sindbis virus of cervical cancer cell lines (Hela and C33A) (1: control (no infection); 2: 1 MOI; 3: 0.1 MOI; 4: 0.01 MOI).
Figure 12:
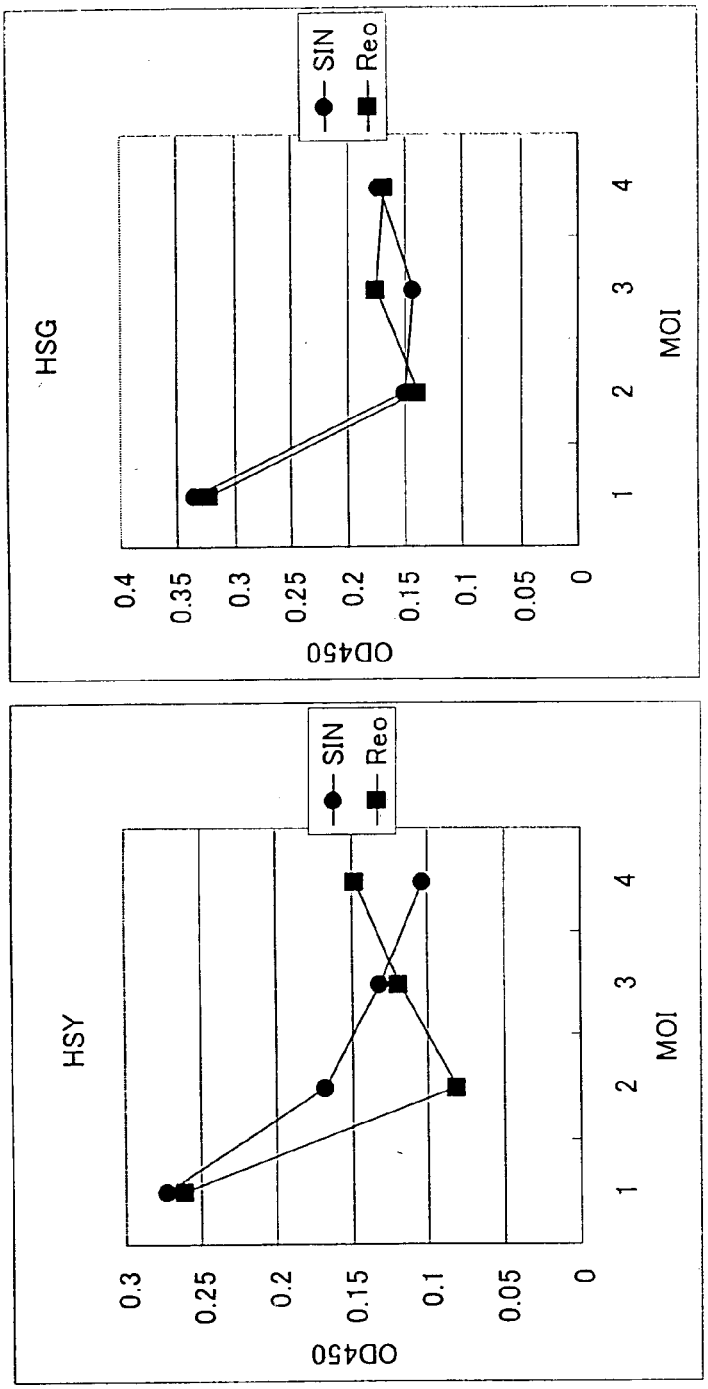
FIG. 12 shows a graph of absorbance at 48 hours after infection with Sindbis virus of a parotid cancer cell line (HSY) and of a salivary gland cancer cell line (HSG) (1: control (no infection); 2: 1 MOI; 3: 0.1 MOI; 4: 0.01 MOI).

In addition, at 48 or 72 hours after virus infection, a culture solution of the aforementioned 24-well plate was removed from the plate and was stained with crystal violet, followed by decolorization with running water. Thereafter, absorbance at 450 nm was measured using Wallac 1420 (Perkin Elmer). In measurement of absorbance also, it was confirmed that Sindbis virus exhibited strong cytopathic effects at an extremely low infectivity titer (0.01 MOI) in all of the following cancer cell lines: immortalized human keratinocytes (EN60: FIG. 6, middle), serum-resistant immortalized human keratinocytes (ENR2: FIG. 6, right), gastric cancer cell lines (MKN45, MKN28, and MKN74: FIG. 7), liver cancer cell lines (HepG2, PLC/PRF/5: FIG. 8), lung cancer cell lines (H358 and A549: FIG. 9), esophageal cancer cell lines (YES-6, TTn, and TE-2: FIG. 10), cervical cancer cell lines (Hela and C33A: FIG. 11), a parotid cancer cell line (HSY: FIG. 12), and a submandibular gland cancer cell line (HSG: FIG. 12). The value described on the graph was the mean value of three independent experiments. All of the standard errors were no more than 15%.

EXAMPLE 2

Figure 13:
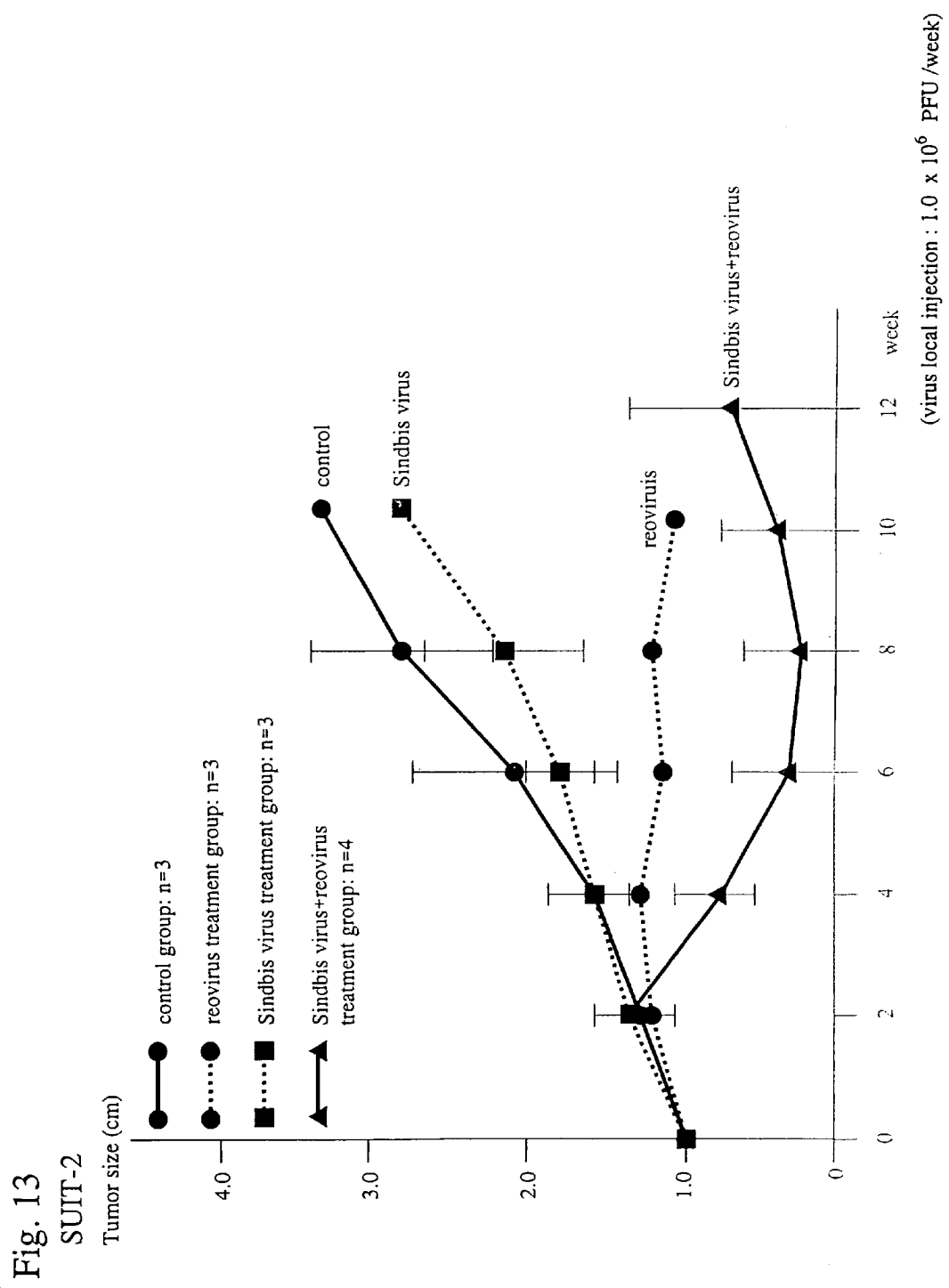
FIG. 13 shows changes over time in the size of tumors which were formed in mice after inoculation of a pancreatic cancer cell line (SUIT-2) during oncolytic therapy with only Sindbis virus, with only reovirus, and with the combined use of Sindbis virus and reovirus.
Figure 14:
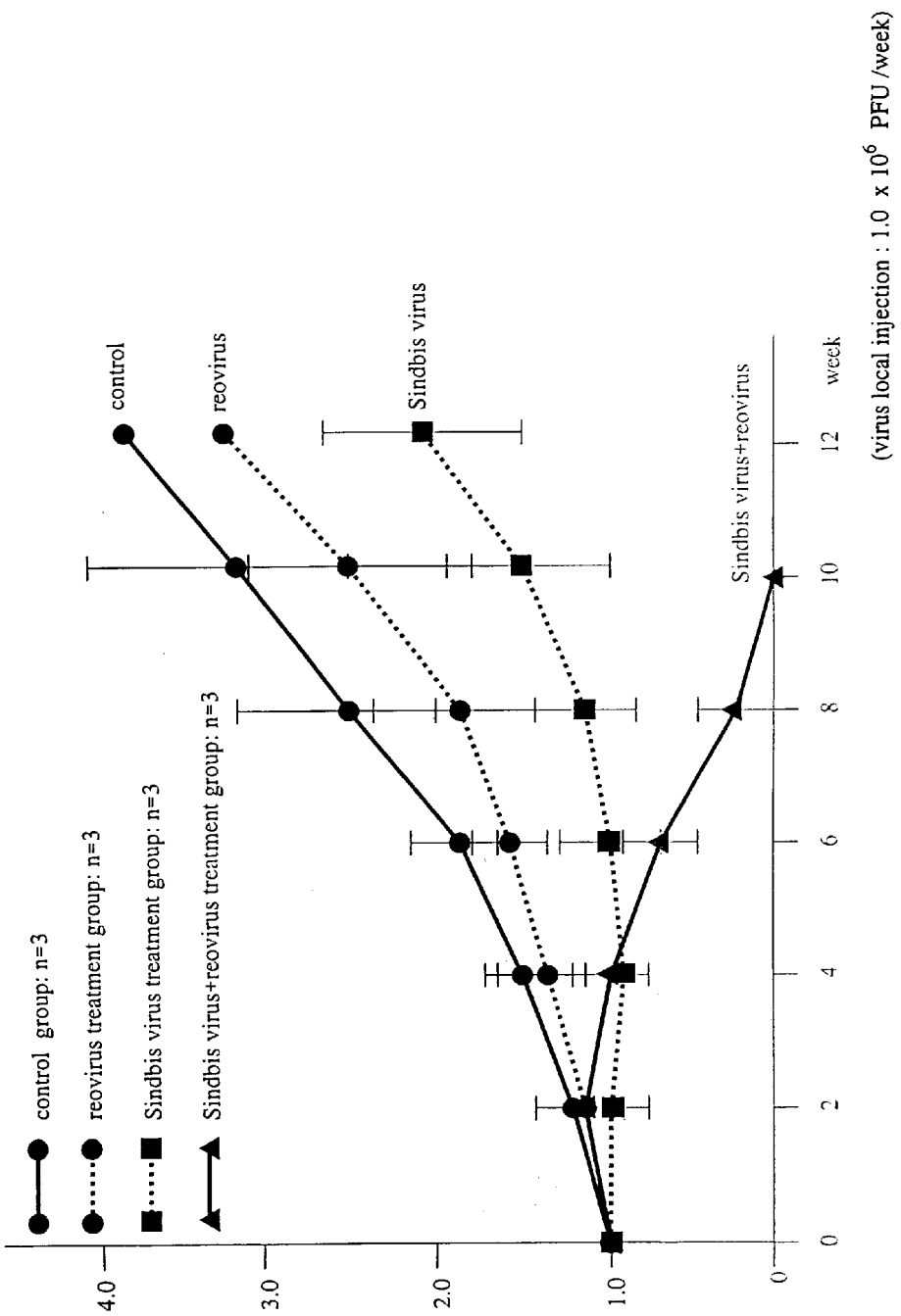
FIG. 14 shows changes over time in the size of tumors which were formed in mice after inoculation of a pancreatic cancer cell line (BxPC-3) during oncolytic therapy with only Sindbis virus, with only reovirus, and with the combined use of Sindbis virus and reovirus.
Figure 15:
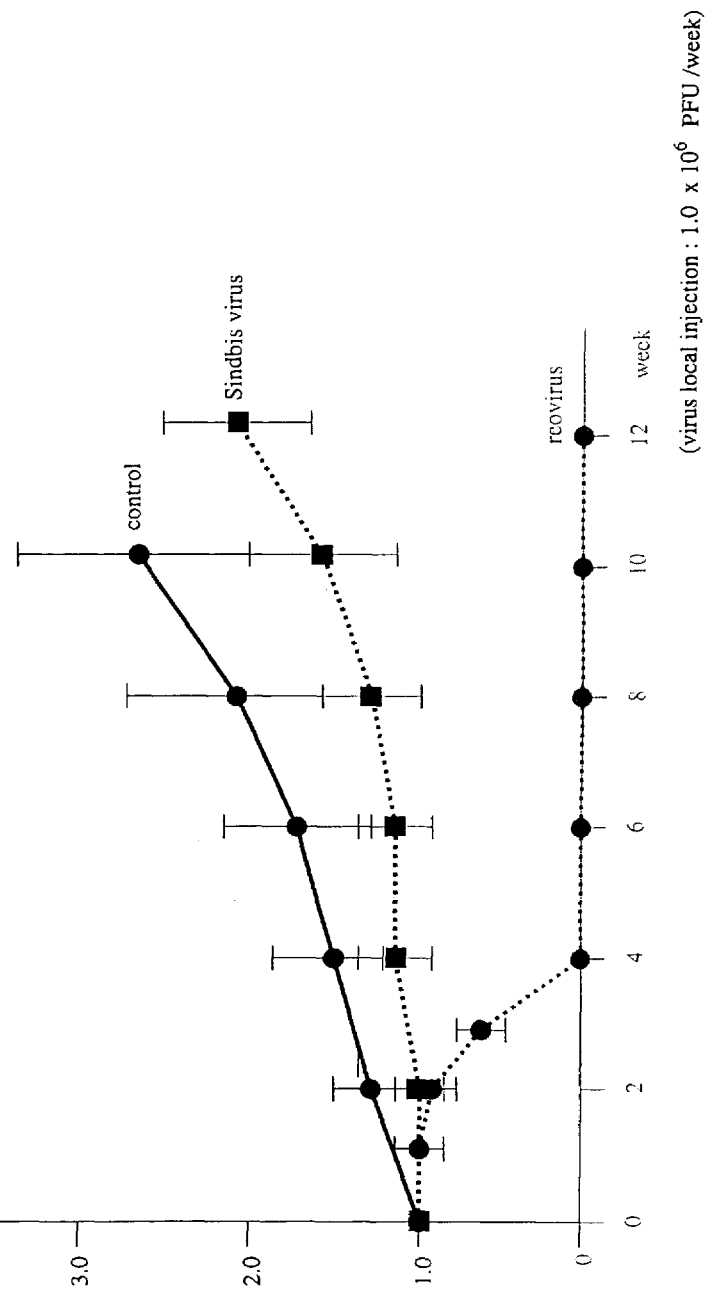
FIG. 15 shows changes over time in the size of tumors which were formed in mice after inoculation of a pancreatic cancer cell line (PANC-1) during oncolytic therapy with only Sindbis virus and with only reovirus.
Figure 16:
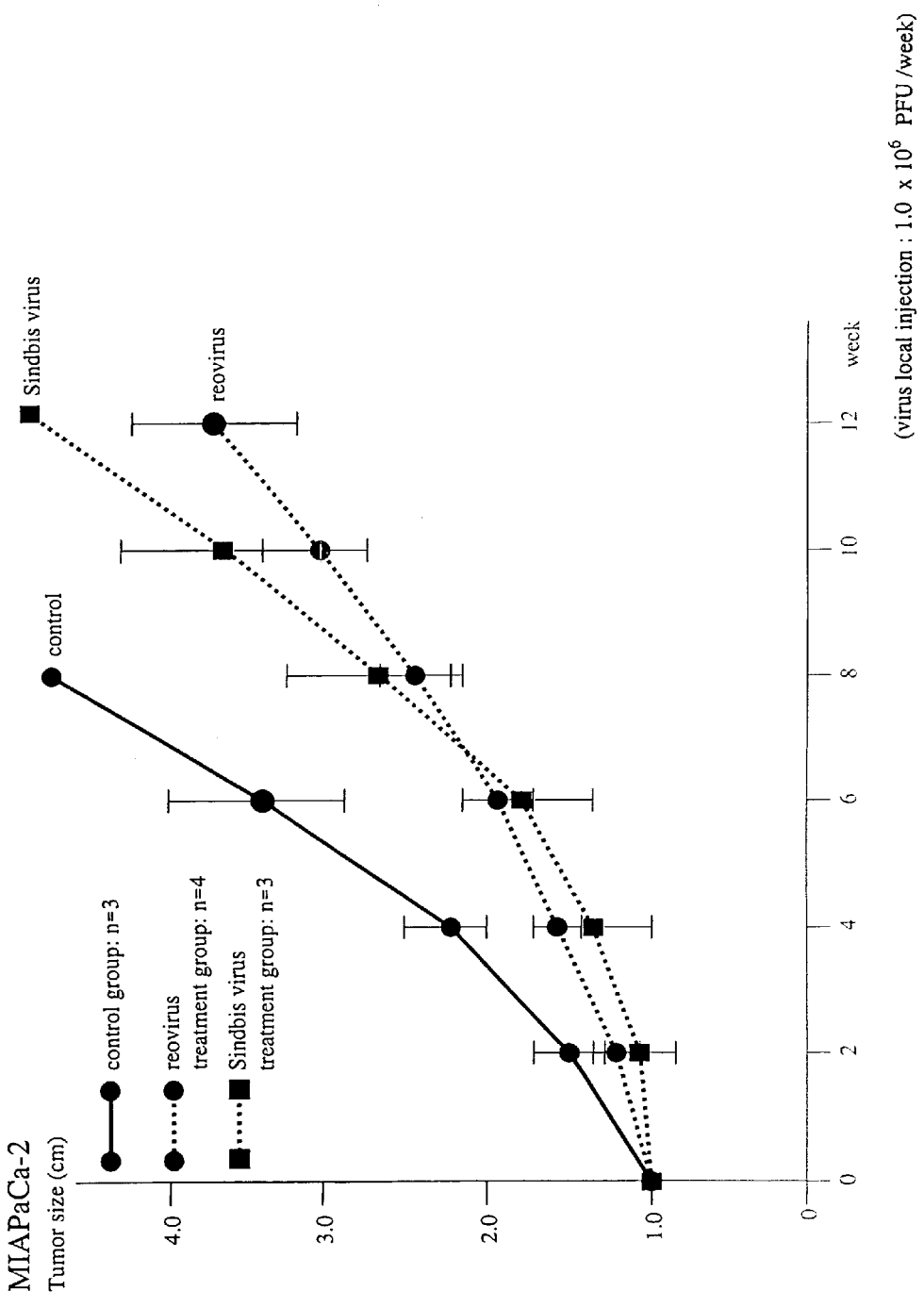
FIG. 16 shows changes over time in the size of tumors which were formed in mice after inoculation of a pancreatic cancer cell line (MIAPaCa-2) during oncolytic therapy with only Sindbis virus and with only reovirus.

In Vivo Examination Regarding Antitumor Effects (1) Pancreatic cancer cell lines (SUIT-2, BxPC-3, PANC-1, and MIAPaCa-2) were subcutaneously inoculated into nude mice (female, 6 to 8 weeks old). When the maximum tumor diameter reached 10 mm, a solution of Sindbis virus or a mixed solution of Sindbis virus and reovirus ($1\times10^6$ PFU) was administered to the tumor once every 7 days. As a result, the reduction in tumor size was confirmed (FIGS. 13 to 16). Synergistic effects of the combined use of Sindbis virus and reovirus were observed in SUIT-2 and Bx-PC (FIGS. 13 and 14).

Figure 17:
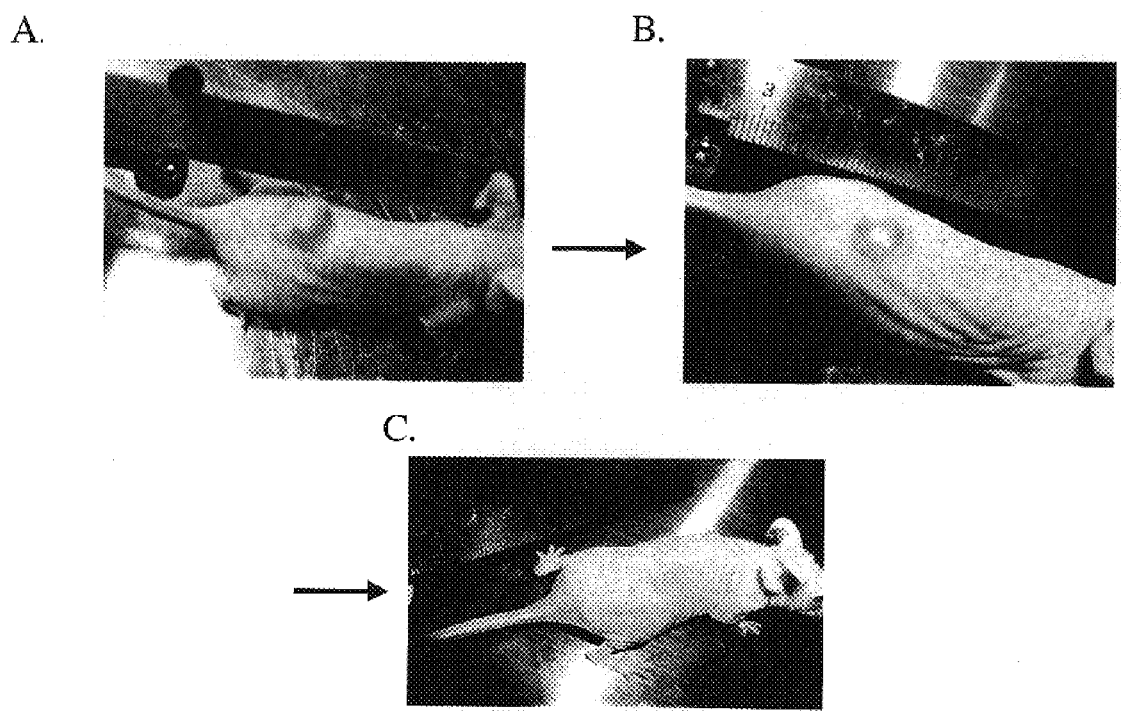
FIG. 17 shows the state of tumors formed in mice after inoculation of a pancreatic cancer cell line (SUIT-2), wherein, during the course of therapy involving once-per-week administration with viruses, only Sindbis virus was administered for the $1^{st}$ and $2^{nd}$ administration ($1.0 \times 10^6$ PFU), only reovirus was administered for the $3^{rd}$ administration ($1.0 \times 10^6$ PFU), and a mixed solution of Sindbis virus and reovirus was administered for the $4^{th}$ and $5^{th}$ administration ($1.0 \times 10^6$ PFU of each virus) (A: the state of tumor immediately before the $3^{rd}$ administration; B: the state of tumor immediately before the $4^{th}$ administration; C: the state of tumor one week after the $5^{th}$ administration).

(2) A pancreatic cancer cell line (SUIT-2) was subcutaneously inoculated into nude mice (female, 6 to 8 weeks old). When the maximum tumor diameter reached 10 mm, the following virus solutions were administered to the tumor once every 7 days. The administered virus solutions consisted of a Sindbis virus solution for the $1^{st}$ and $2^{nd}$ administrations ($1\times10^6$ PFU), a reovirus solution for the $3^{rd}$ administration ($1\times10^6$ PFU), and a mixed solution of Sindbis virus and reovirus for the $4^{th}$ and $5^{th}$ administrations ($1\times10^6$ PFU). Morphological observation of tumor was conducted immediately before administration of the above solutions every week. The tumor status was shown in photographs taken immediately before the $3^{rd}$ administration (FIG. 17A), immediately before the $4^{th}$ administration (FIG. 17B), and 1 week after the $5^{th}$ administration (FIG. 17C). At each time, reduction in tumor size was observed, and thus, the synergetic effect of the combined use of Sindbis virus and reovirus was confirmed (FIG. 17A: immediately before the $3^{rd}$ administration; FIG. 17B: immediately before the $4^{th}$ administration; FIG. 17C: 1 week after the $5^{th}$ administration).

Evident cytotoxicity to normal tissues was not observed, in either the short term or the long term, in the nude mice to which Sindbis virus had been subcutaneously administered. The nude mice in which tumors had disappeared have been in very good health and have been living more than 6 months to date.

EXAMPLE 3

TUNEL Assay

For the purpose of elucidating whether or not cytopathic effects exhibited by Sindbis virus (SIN) indicate apoptosis, an esophageal cancer cell line TTn was infected with SIN at 1 MOI for 24 hours, followed by detection of apoptosis cells using the terminal transferase uridyl nick end labelling (TUNEL) assay.

TTn cells were grown on Lab-TeK chamber slides (Nalge Nunc International) and infected with SIN at 1 MOI for 24 hours. The cells were washed with phosphate-buffered saline (PBS) and then fixed in 4% paraformaldehyde at 4° C. for 30 minutes. The TUNEL assay was performed using an In situ Apoptosis Detection Kit (Takara, Tokyo, Japan) according to the manufacturer's instruction. Specifically, the fixed cells were incubated with 100 µl of Permeabilization buffer at 4° C. for 5 minutes and subsequently reacted at 37° C. for 60 minutes with the mixture of 5 µl of TdT enzyme and 45 µl of labeling safe buffer containing FITC-dUTP. These samples were examined using a fluorescence microscope (Nikon Inc., Tokyo, Japan).

Figure 18:
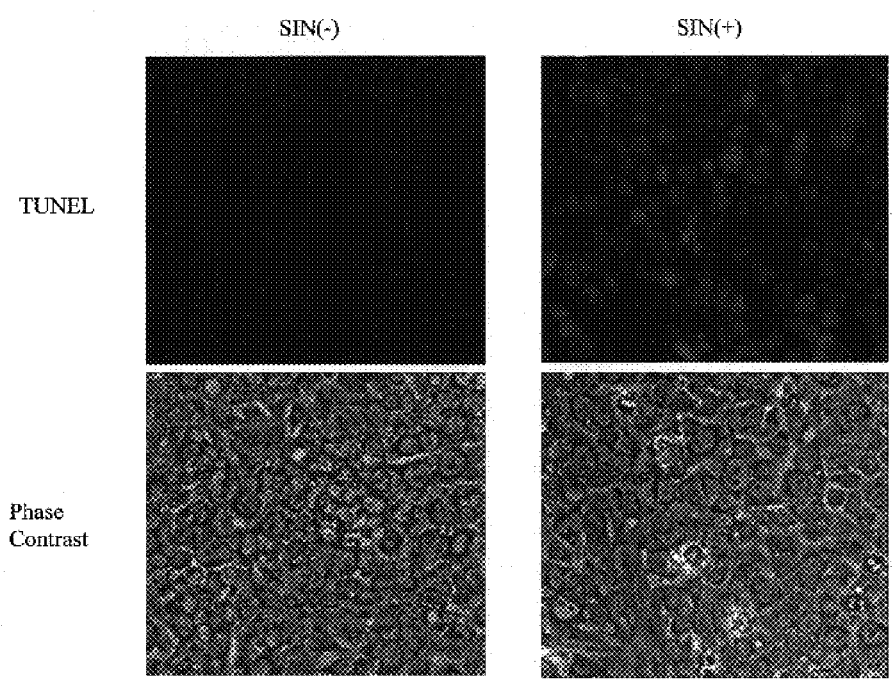
FIG. 18 shows the results of TUNEL assay on TTn cells infected with Sindbis virus.

The results are shown in FIG. 18. Almost all SIN-infected TTn cells (SIN(+)) became TUNEL positive. However, there was substantially no TUNEL positive cells among SIN-noninfected TTn cells (SIN(−)).

EXAMPLE 4

Western Blot Analysis

A cervical cancer cell line (Hela and C33A), primary human keratinocytes, and Vero cells as control cells were infected with Sindbis virus, thereby examining the expression of a virus protein by Western blot analysis.

(1) Preparation of Anti-SIN Antibody

A solution of Sindbis virus was subcutaneously administered to the back of a rabbit. Such immunization was repeated 4 times every 2 weeks. Two weeks after the first immunization, blood samples were obtained, and then sampled every two weeks. The serums (containing anti-SIN antibodies) of samples were separated and stored at −70° C. before use.

(2) Protein Extraction and Western Blot Analysis

Cells, cultured in a 10 cm-diameter dish, were infected with SIN at 0.1 MOI. At indicated times (0, 12, 24, and 48 hours) after the infection, the cells were washed with PBS and lysed in the whole cell extract (WCE) buffer containing 20 mM HEPES, 75 mM NaCl, 2.5 mM $MgCl_2$, 0.1 mM EDTA, 0.05% TritonX-100, 0.5 mM DTT, 0.1 mM $NaVO_4$, 2 µg of leupeptin, and 100 µg of PMSF per ml. The lysates were frozen and cleared of debris by centrifugation. The supernatants were mixed with SDS-PAGE sample buffer and boiled for 2 min. The samples (200 µg, each) were subjected to SDS-PAGE (12% acrylamide gel) and electrophoretically transferred to a polyvinylidene difluoride (PVDF) membrane filter.

Membrane filters were blocked by incubation with 5% dry milk in phosphate-buffered saline (PBS) solution and 0.05% tween 20 (PBST) for 1 hour at room temperature, followed by overnight incubation at 4° C. with the anti-SIN antibody in a blocking buffer. After washing three times, the filters were incubated with HRP-conjugated secondary antibodies for 1 hour at 4° C., followed by another thorough wash in PBST. The blots were developed with an enhanced chemiluminescent ECL® Plus detection kit (Amersham) according to the manufacturer's instruction. Detection was performed using Fluor-S MultiImager (Bio-Rad Laboratories).

Figure 19:
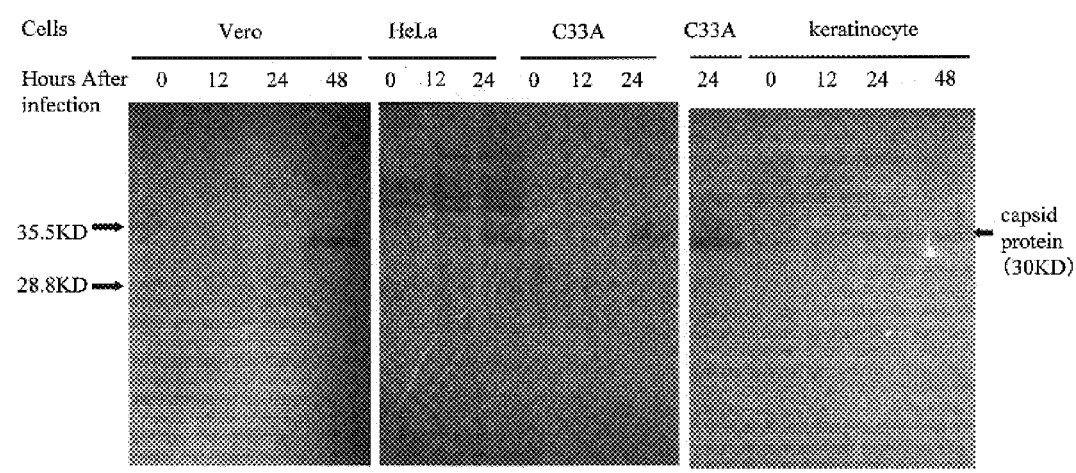
FIG. 19 shows the results of Western blot analysis of the expression of a Sindbis virus protein in keratinocytes, Vero cells, and cancer cell lines (Hela and C33A).

The results are shown in FIG. 19. Expression of a virus protein was confirmed in the control Vero cells after 48 hours. In Hela cells and C33A cells, clear expression was confirmed after 24 hours. No expression was identified in primary human keratinocytes.

EXAMPLE 5

Virus Growth Assays in Human Keratinocytes and Cancer Cells

Primary culture keratiocytes, immortalized keratinocytes (EN60), esophageal cancer cell lines (YES-6 and TTn), and cervical cancer cell lines (Hela and C33A) were infected with Sindbis virus at 0.1 MOI for 48 hours. Each culture supernatant was collected, and virus titer in a medium was determined by the standard plaque assays using monolayers of BHK-21 cells.

Figure 20:
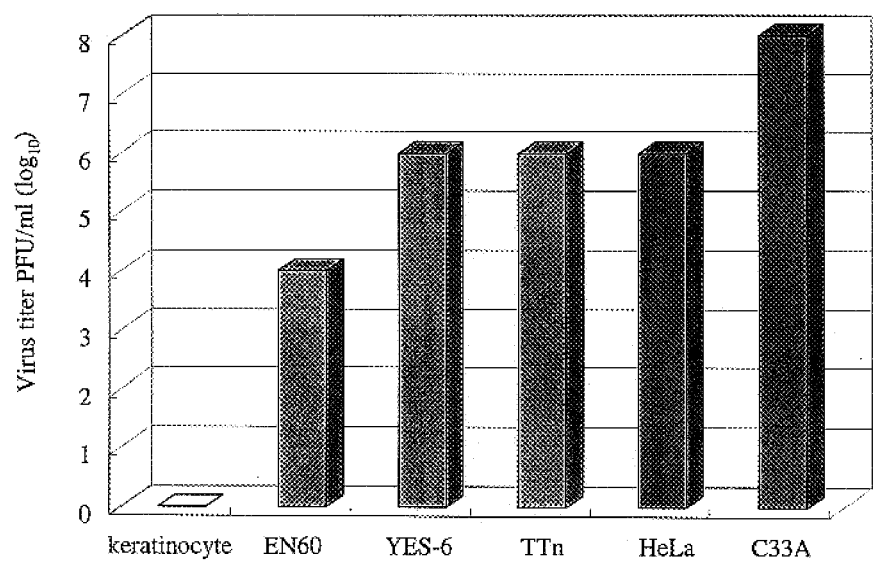
FIG. 20 shows a titer of Sindbis virus in keratinocytes, immortalized keratinocytes (EN60), and cancer cell lines (YES-6, TTn, Hela, and C33A).

The results are shown in FIG. 20. The growth of the virus was not observed in primary human keratinocytes, but it was observed in immortalized human keratinocytes. A solution of high-titer virus was obtained from four types of cancer cells. Thereafter, two individual experiments were carried out. From these experiments, similar results were obtained.

EXAMPLE 6

Xenograft Model in Mice

All animal experiments were conducted in accordance with the Chiba University laboratory animal center guidelines. To induce subcutaneous tumors, $5 \times 10^6$ TTn and $1 \times 10^7$ YES-6 cells were injected subcutaneously into the back of SCID mice, and $1 \times 10^7$ C33A cells were similarly injected into BALA/c nude mice. All mice were 6-week-old females purchased from Charles River Japan. Inc.

Figure 21:
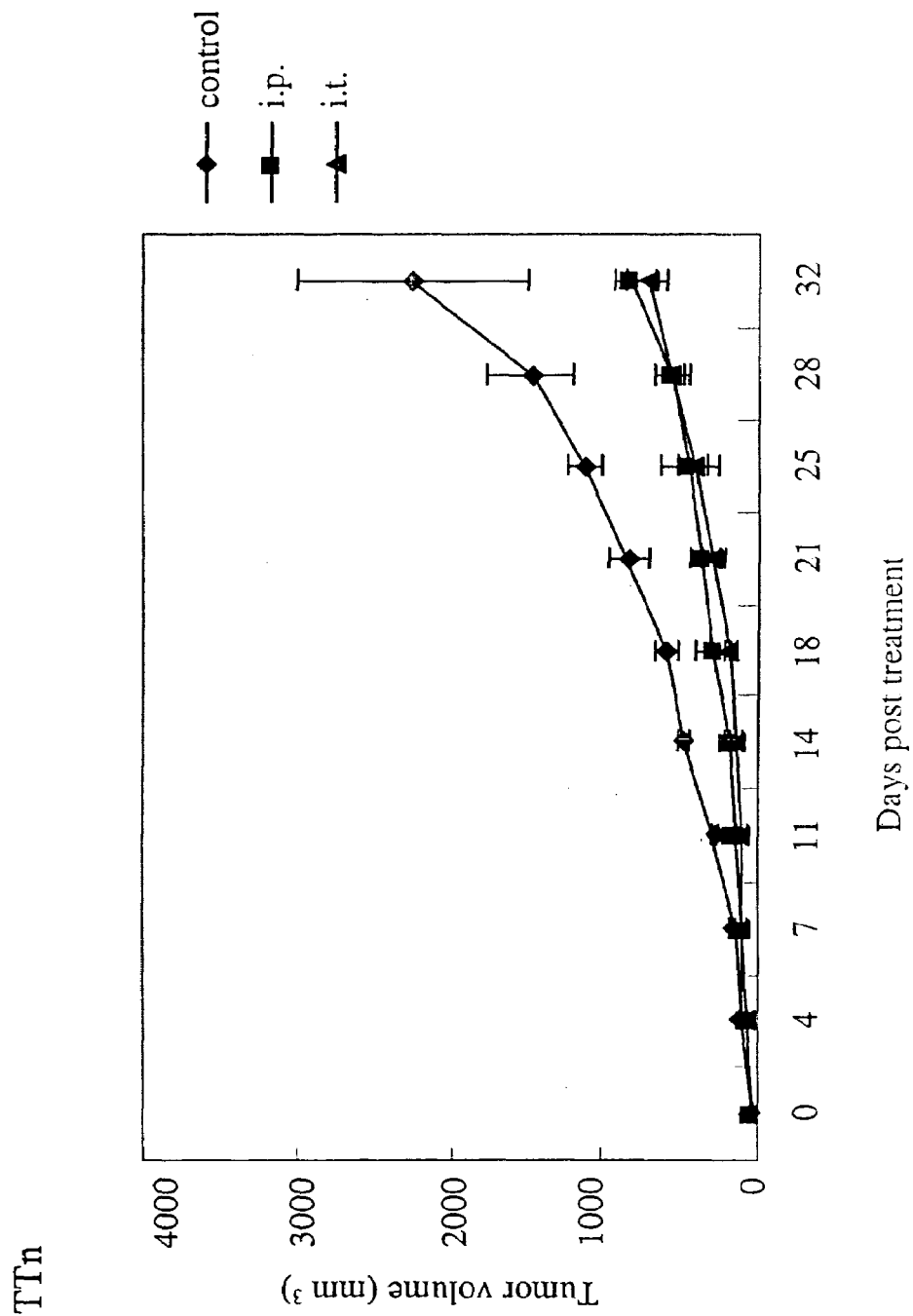
FIG. 21 shows the change in tumor size of TTn tumors on the back of mice intraperitoneally or intratumorally administered with Sindbis virus (control: no administration; i.p.: intraperitoneal administration; i.t.: intratumoral administration).
Figure 22:
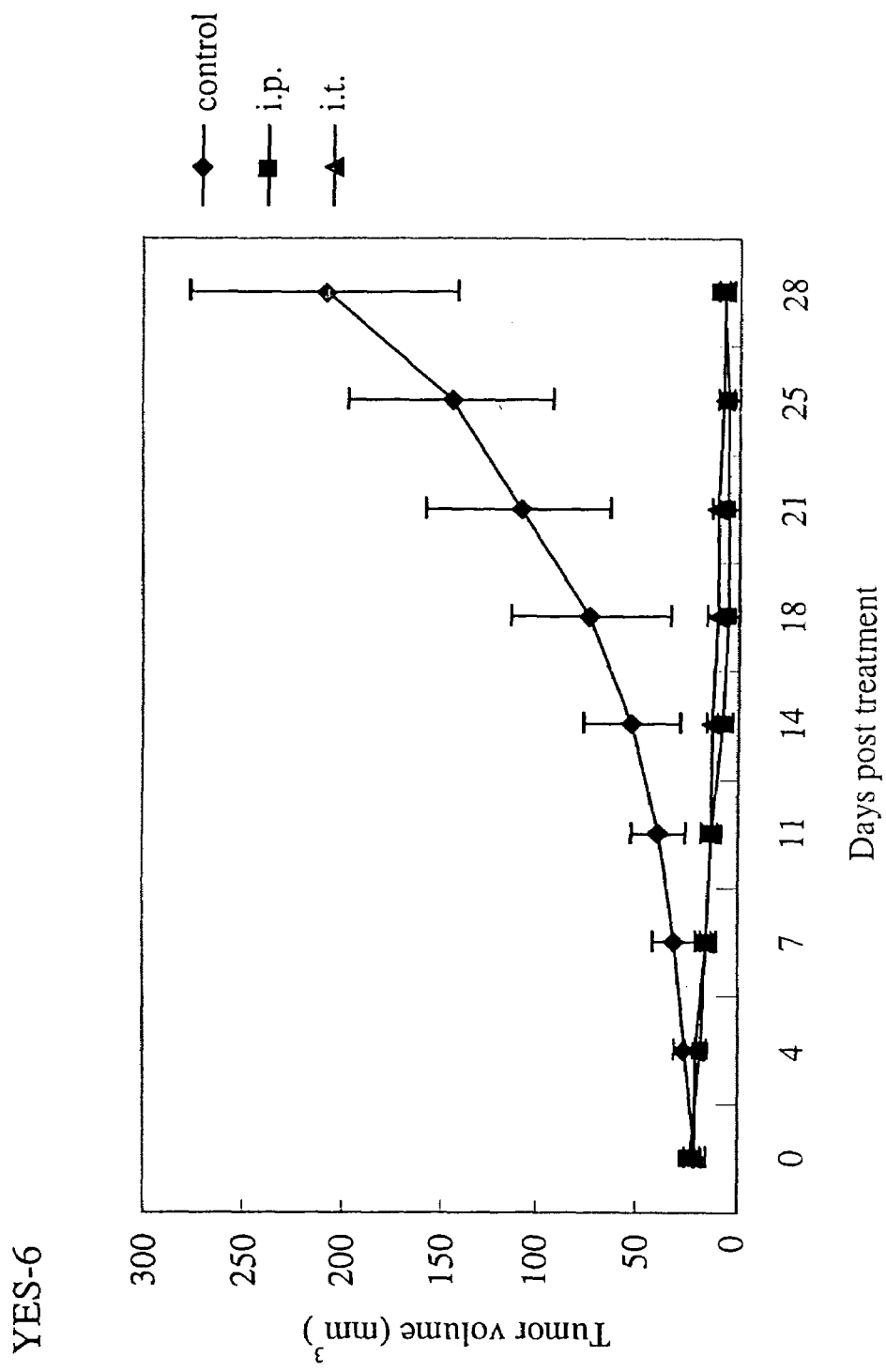
FIG. 22 shows the change in tumor size of YES-6 tumors on the back of mice intraperitoneally or intratumorally administered with Sindbis virus (control: no administration; i.p.: intraperitoneal administration; i.t.: intratumoral administration).
Figure 23:
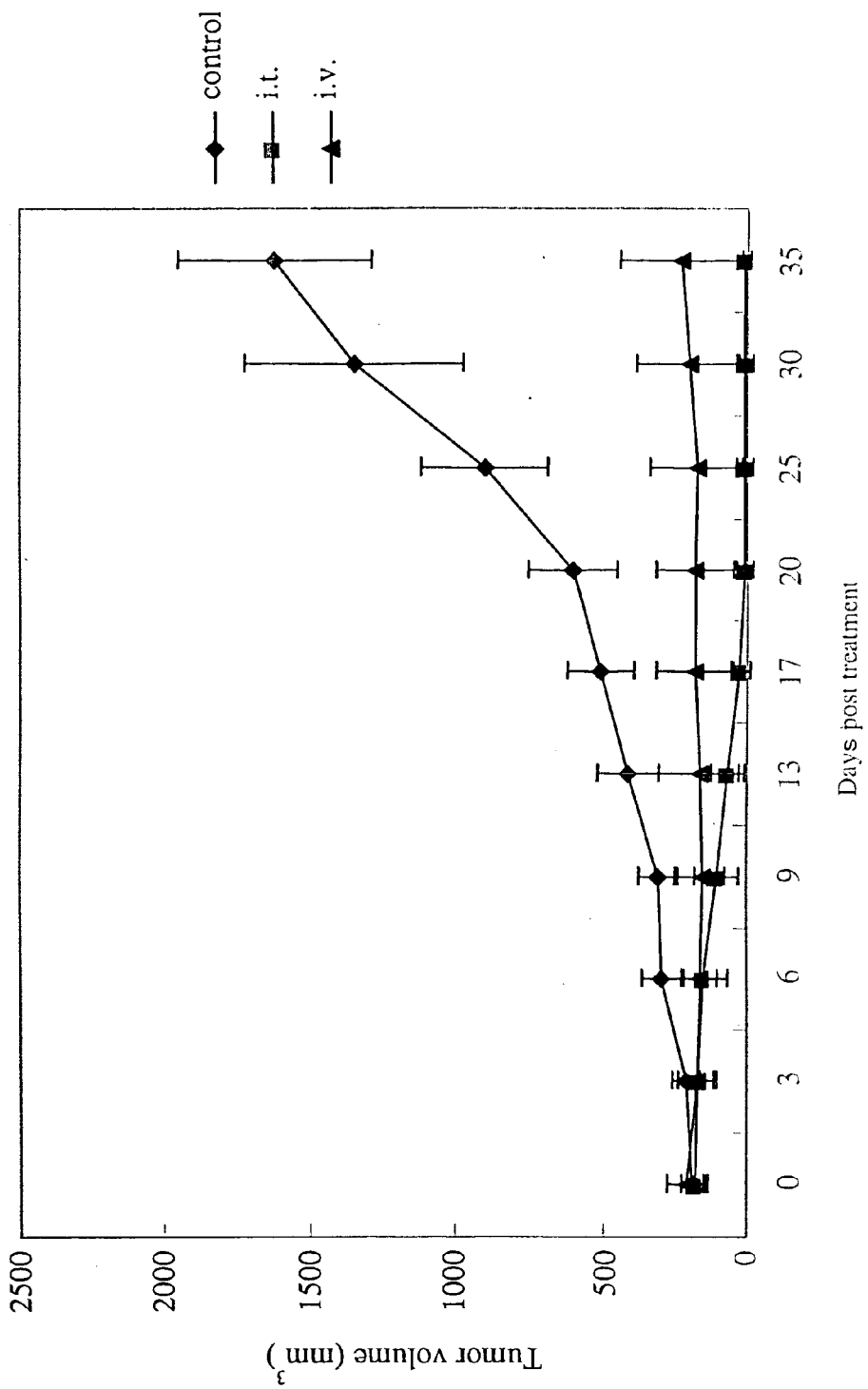
FIG. 23 shows the change in tumor size of C33A tumors on the back of mice intravenously or intratumorally administered with Sindbis virus (control: no administration; i.v.: intravenous administration; i.t.: intratumoral administration).

When the diameter of the tumor derived from TTn cells reached 5 mm, mice were intratumorally (i.t.) and intraperitoneally (i.p.) injected with $5 \times 10^7$ PFU of SIN. When the diameter of the tumor derived from YES-6 cells reached 7 mm, mice were intratumorally (i.t.) and intraperitoneally (i.p.) injected with $1 \times 10^6$ PFU of SIN. When the diameter of the tumor derived from C33A cells reached 7 mm, mice were intratumorally (i.t.) and intravenously (i.v.) injected with $1 \times 10^6$ PFU of SIN. Injections were repeated every 3 or 4 days after the measurement of tumor size using calipers. Changes in tumor size after administration of SIN to TTn, YES-6, and C33A cells are shown in FIGS. 21 to 23, respectively. The tumor size was calculated as: (long axis)×(short axis)×(height). Significant reduction in the size of tumor was observed in all test animals (4 samples for each administration) in all the routes of administration.

EXAMPLE 7

In Vivo GFP Imaging

A C33A cell line was subcutaneously inoculated to BALA/c nude mice. When the diameter of tumor reached 7 mm, $10^6$ PFU of GFP-expressing SIN (GFP-SIN) was injected into the jugular vein of the mice. GFP-expression in tumor was examined every 12 hours after the injection using an Oympus fluorescence stereo microscope (model SZX7) equipped with a reflected light fluorescence unit for GFP (SZX-RFL2-GFP), which was coupled with a Hamamatsu ORCA-ER cooled CCD camera.

Figure 24:
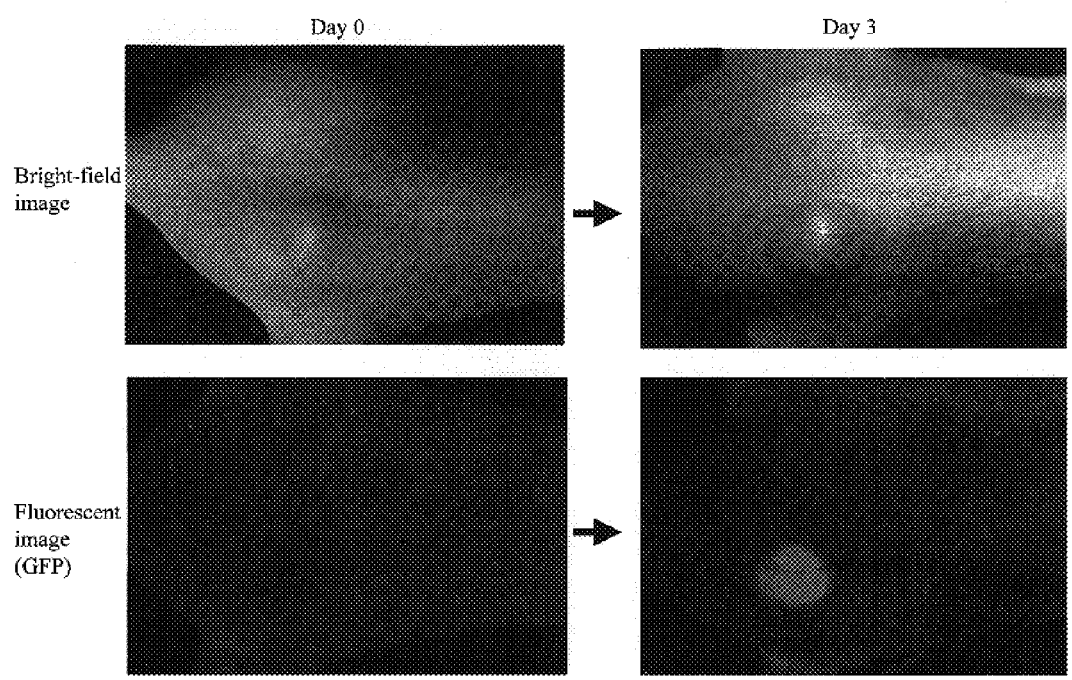
FIG. 24 shows the bright-field and fluorescent images of C33A tumors on the back of a mouse intravenously injected with green fluorescent protein (GFP)-expressing recombinant Sindbis virus (GFP-SIN) at day 0 (Day 0) and day 3 (Day 3) post-injection.
Figure 25:
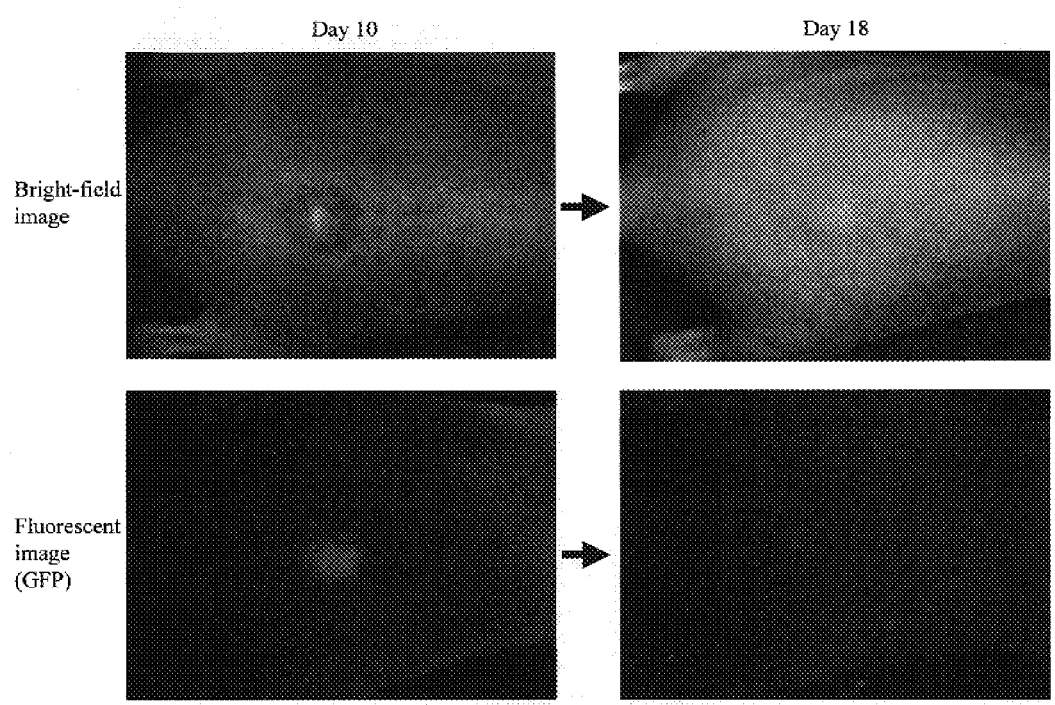
FIG. 25 shows the bright-field and fluorescent images of C33A tumors on the back of a mouse intravenously injected with GFP-SIN at day 10 (Day 10) and day 18 (Day 18) post-injection.
Figure 26:
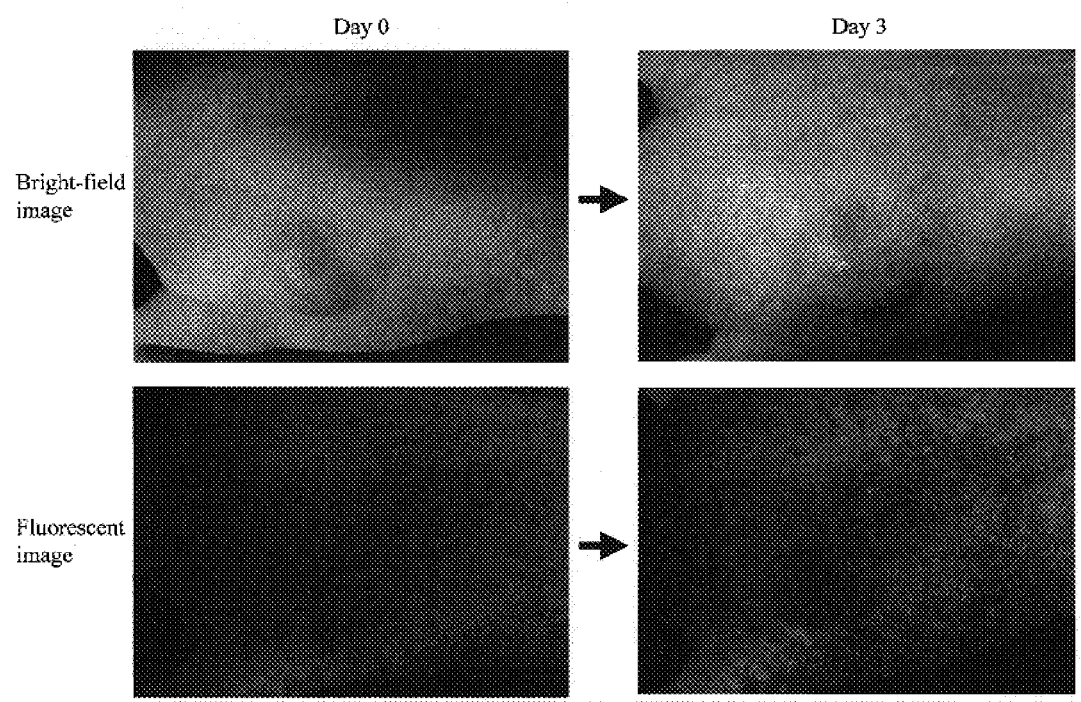
FIG. 26 shows the bright-field and fluorescent images of C33A tumors on the back of a mouse intravenously injected with only a SIN-free medium at day 0 (Day 0) and day 3 (Day 3) post-injection.
Figure 27:
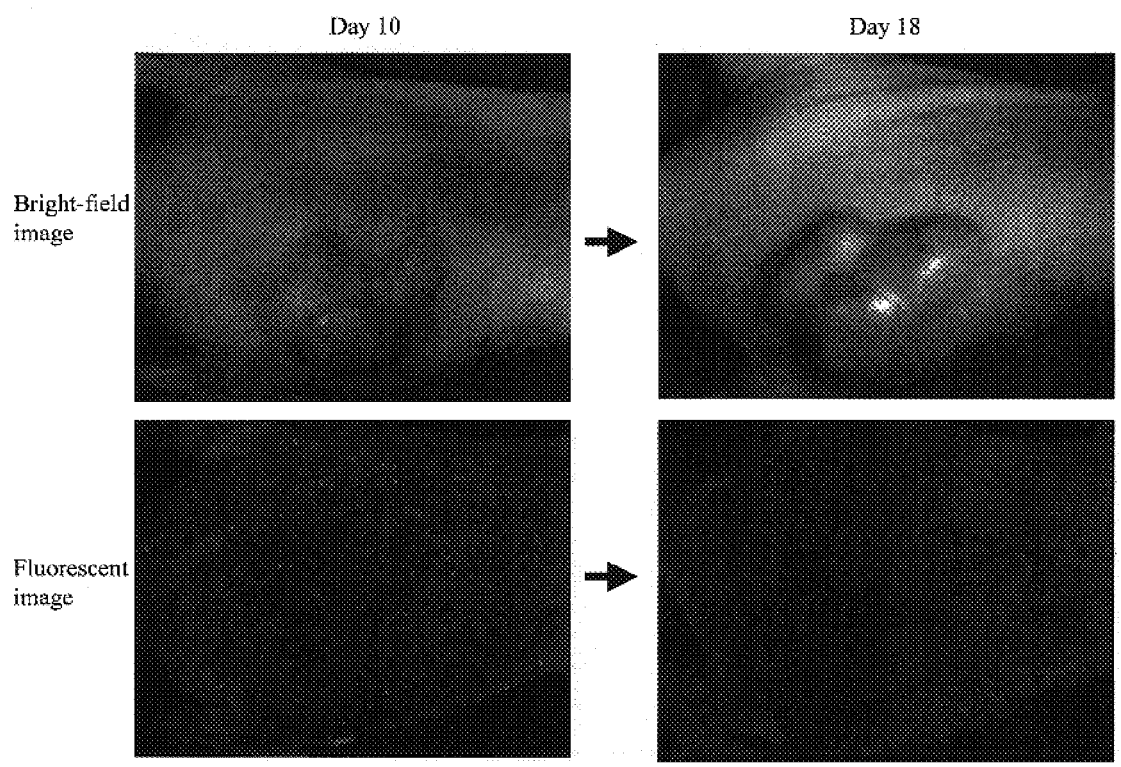
FIG. 27 shows the bright-field and fluorescent images of C33A tumor on the back of a mouse intravenously injected with only a SIN-free medium at day 10 (Day 10) and day 18 (Day 18) post-injection

In a GFP-SIN administration group, tumors partially became GFP-positive in all samples (9 cases) at 36 hours after the administration. Substantially all portion of tumor became GFP-positive at 72 hours (3 days) after the administration. Typical examples of changes over time are shown in FIGS. 24 and 25. The expression was observed for more than 2 weeks (for 9 to 20 days in other cases). The GFP expression faded coincident with disappearance of tumor. In contrast, tumors did not become GFP-positive in a control group to which only a SIN-free medium was administered, and an obvious growing trend was shown in the tumors (FIGS. 26 and 27).

EXAMPLE 8

Analysis of GFP Expression in Tissues of GFP-SIN-Injected Mice

Figure 28:
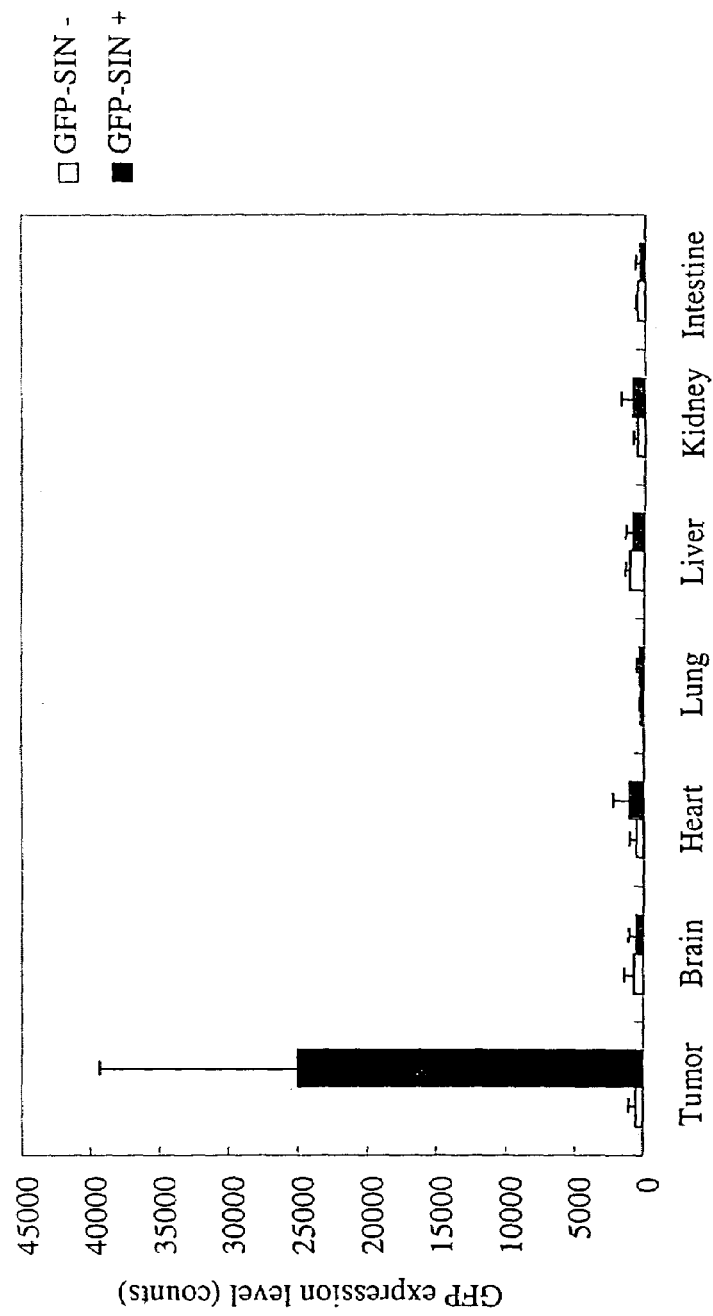
FIG. 28 shows the expression levels of GFP in tumors and each organ of mice treated with GFP-SIN (GFP-SIN+) or SIN-free medium (GFP-SIN−).

A C33A cell line was subcutaneously inoculated to BALA/c nude mice. When tumor diameter reached 7 mm, 1×10 PFU of GFP-SIN was administered in the same manner as in Example 7. Seventy-two hours after the injection the mice were sacrificed, and tumors and organs thereof were collected. Tissues (20 mg) from tumors and organs (brain, heart, lung, liver, kidney, and intestine) were excised, and 20 mg each of the tissues were homogenized by sonication, followed by observation of the level of GFP expression with Wallac 1420 ARVOsx (Perkin Elmer). The results are shown in FIG. 28. In the figure, the analyzed results of three samples from SIN treatment groups (GFP-SIN+) and non-treatment groups (GFP-SIN−) were averaged. (Error bar denotes standard deviation.) Thus, it was revealed that GFP-SIN expression was observed in a tumor-specific manner.

All publications, patents, and patent applications cited herein are incorporated herein by reference in their entirety.

INDUSTRIAL APPLICABILITY

Sindbis virus infects tumor cells to grow specifically therein, and exerts significant action for reduction or disappearance of tumor. In addition, Sindbis virus exhibits cytopathic effects in cancer cells having no mutation in the K-Ras gene, thereby exerting antitumor action for a broad range of cancers at a low infectivity titer. Furthermore, Sindbis virus has no side effects on human bodies, and there is no need to conduct gene modification in order to obtain the above effects. Therefore, Sindbis virus is highly safe and can be applied for less invasive treatment of cancers.

A pharmaceutical composition for treatment of cancers is clinically very useful as a medicament for treating cancers such as cervical cancer, esophageal cancer, gastric cancer, and liver cancer.

What is claimed is:

1. A pharmaceutical composition for treating pancreatic cancer, which comprises Sindbis virus and reovirus as an active component.

2. The pharmaceutical composition according to claim 1, which comprises at least one strain of Sindbis virus.

3. The pharmaceutical composition according to claim 1, wherein the Sindbis virus is Sindbis virus AR339.

4. A method for the treatment of pancreatic cancer, which comprises
   administering to a mammal having pancreatic cancer a therapeutically effective amount of Sindbis virus and reovirus, whereby tumor size is reduced.

5. The method according to claim 4, wherein at least one strain of Sindbis virus is administered.

6. The method according to claim 4, wherein the Sindbis virus is Sindbis virus AR339.

7. The method according to claim 4, wherein the Sindbis virus is administered intravenously, intraarterially, intramuscularly, intraperitoneally, subcutaneously, topically, intratumorally, orally, transdermally, rectally, intravaginally, intranasally, or sublingually.

8. The method according to claim 4, wherein 0.01 to $1 \times 10^{15}$ plaque forming units (PFU) of Sindbis virus per kilogram of body weight are administered.

* * * * *